(12) United States Patent
Smith et al.

(10) Patent No.: US 12,351,839 B2
(45) Date of Patent: *Jul. 8, 2025

(54) RATIONALLY-DESIGNED SINGLE-CHAIN MEGANUCLEASES WITH NON-PALINDROMIC RECOGNITION SEQUENCES

(71) Applicant: Precision Biosciences, Inc., Durham, NC (US)

(72) Inventors: James Jefferson Smith, Morrisville, NC (US); Derek Jantz, Durham, NC (US)

(73) Assignee: Precision BioSciences, Inc., Durham, NC (US)

( * ) Notice: Subject to any disclaimer, the term of this patent is extended or adjusted under 35 U.S.C. 154(b) by 19 days.

This patent is subject to a terminal disclaimer.

(21) Appl. No.: 18/185,726

(22) Filed: Mar. 17, 2023

(65) Prior Publication Data

US 2023/0416711 A1 Dec. 28, 2023

Related U.S. Application Data

(63) Continuation of application No. 17/079,377, filed on Oct. 23, 2020, now abandoned, which is a continuation of application No. 16/025,747, filed on Jul. 2, 2018, now abandoned, which is a continuation of application No. 15/132,941, filed on Apr. 19, 2016, now Pat. No. 10,041,053, which is a continuation of application No. 14/858,986, filed on Sep. 18, 2015, now Pat. No. 9,340,777, which is a continuation of application No. 14/723,840, filed on May 28, 2015, now abandoned, which is a continuation of application No. 13/897,923, filed on May 20, 2013, now abandoned, which is a continuation of application No. 12/771,163, filed on Apr. 30, 2010, now Pat. No. 8,445,251, which is a continuation of application No. PCT/US2008/082072, filed on Oct. 31, 2008.

(60) Provisional application No. 61/001,247, filed on Oct. 31, 2007.

(51) Int. Cl.
| | | |
|---|---|---|
| C12N 9/22 | (2006.01) |
| A61P 31/00 | (2006.01) |
| A61P 31/04 | (2006.01) |
| A61P 31/12 | (2006.01) |
| A61P 33/02 | (2006.01) |
| A61P 43/00 | (2006.01) |
| C12N 9/16 | (2006.01) |
| C12N 15/85 | (2006.01) |
| C12N 15/90 | (2006.01) |

(52) U.S. Cl.
CPC ................. *C12N 9/22* (2013.01); *C12N 9/16* (2013.01); *C12N 15/8509* (2013.01); *C12N 15/902* (2013.01); *C12N 15/907* (2013.01); *C12N 2800/80* (2013.01); *C12Y 301/00* (2013.01); *C12Y 301/04* (2013.01)

(58) Field of Classification Search
None
See application file for complete search history.

(56) References Cited

U.S. PATENT DOCUMENTS

| | | |
|---|---|---|
| 4,873,316 A | 10/1989 | Meade et al. |
| 5,384,253 A | 1/1995 | Krzyzek et al. |
| 6,316,024 B1 | 11/2001 | Allen et al. |
| 6,379,699 B1 | 4/2002 | Virtanen et al. |
| 6,387,397 B1 | 5/2002 | Chen et al. |
| 6,511,676 B1 | 1/2003 | Boulikas |
| 6,593,308 B2 | 7/2003 | Szoka, Jr. |
| 7,037,492 B2 | 5/2006 | Glorioso et al. |
| 7,897,372 B2 | 3/2011 | Duchateau et al. |
| 8,119,361 B2 | 2/2012 | Smith et al. |
| 8,124,369 B2 | 2/2012 | Smith et al. |
| 8,129,134 B2 | 3/2012 | Smith et al. |
| 8,133,697 B2 | 3/2012 | Smith et al. |
| 8,143,015 B2 | 3/2012 | Smith et al. |
| 8,143,016 B2 | 3/2012 | Smith et al. |
| 8,148,098 B2 | 4/2012 | Smith et al. |
| 8,163,514 B2 | 4/2012 | Smith et al. |
| 8,445,251 B2 | 5/2013 | Smith et al. |
| 9,340,777 B2 | 5/2016 | Smith et al. |
| 9,434,931 B2 | 9/2016 | Smith et al. |
| 10,041,053 B2 | 8/2018 | Smith et al. |

(Continued)

FOREIGN PATENT DOCUMENTS

| | | |
|---|---|---|
| EP | 0 264 166 A1 | 4/1988 |
| JP | 2005-520519 A | 7/2005 |

(Continued)

OTHER PUBLICATIONS

Supplementary European Search Report for European Patent Application No. 08845549.8 dated Dec. 6, 2010. 10 pages.

(Continued)

*Primary Examiner* — Suzanne M Noakes
*Assistant Examiner* — Jae W Lee
(74) *Attorney, Agent, or Firm* — Womble Bond Dickinson (US) LLP

(57) ABSTRACT

Disclosed are rationally-designed, non-naturally-occurring meganucleases in which a pair of enzyme subunits having specificity for different recognition sequence half-sites are joined into a single polypeptide to form a functional heterodimer with a non-palindromic recognition sequence. The invention also relates to methods of producing such meganucleases, and methods of producing recombinant nucleic acids and organisms using such meganucleases.

11 Claims, 1 Drawing Sheet
Specification includes a Sequence Listing.

(56) References Cited

U.S. PATENT DOCUMENTS

| | | |
|---|---|---|
| 2004/0002092 A1 | 1/2004 | Arnould et al. |
| 2006/0078552 A1 | 4/2006 | Arnould et al. |
| 2013/0267009 A1 | 10/2013 | Smith et al. |
| 2015/0337335 A1 | 11/2015 | Smith et al. |

FOREIGN PATENT DOCUMENTS

| | | |
|---|---|---|
| WO | WO 2002/99105 A2 | 12/2002 |
| WO | WO 2003/078619 A1 | 9/2003 |
| WO | WO 2004/067736 A2 | 8/2004 |
| WO | WO 2004/067753 A2 | 8/2004 |
| WO | WO 2005/105989 A1 | 11/2005 |
| WO | WO 2006/097784 A1 | 9/2006 |
| WO | WO 2006/097853 A1 | 9/2006 |
| WO | WO 2006/097854 A1 | 9/2006 |
| WO | WO 2007/034262 A1 | 3/2007 |
| WO | WO 2007/047859 A2 | 4/2007 |
| WO | WO 2007/049095 A1 | 5/2007 |
| WO | WO 2007/049156 A2 | 5/2007 |
| WO | WO 2007/057781 A2 | 5/2007 |
| WO | WO 2007/060495 A1 | 5/2007 |
| WO | WO 2007/093836 A1 | 8/2007 |
| WO | WO 2007/093918 A2 | 8/2007 |
| WO | WO 2008/010009 A1 | 1/2008 |
| WO | WO 2008/059317 A1 | 5/2008 |
| WO | WO 2008/059382 A2 | 5/2008 |
| WO | WO 2008/093152 A1 | 8/2008 |
| WO | WO 2008/093249 A2 | 8/2008 |
| WO | WO 2008/102198 A1 | 8/2008 |
| WO | WO 2008/102274 A2 | 8/2008 |
| WO | WO 2008/152523 A1 | 12/2008 |
| WO | WO 2009/006297 A2 | 1/2009 |
| WO | WO 2009/059195 A2 | 5/2009 |
| WO | WO 2009/074873 A1 | 6/2009 |
| WO | WO 2009/095793 A1 | 8/2009 |

OTHER PUBLICATIONS

Partial European Search Report for EP Application No. 19167904.2 mailed Nov. 12, 2019.
Extended European Search Report for European Patent Application No. 19167904.2 dated Feb. 13, 2020. 19 pages.
International Search Report and Written Opinion issued for PCT/US2008/082072, dated Jul. 20, 2009. 12 pages.
International Preliminary Report on Patentability issued for PCT/US2008/082072, dated May 4, 2010. 7 pages.
Adler, David A. et al. "Bioinformatics." Encyclopedia of Life Sciences. John Wiley & Sons Ltd. No month listed—2001, pp. 1-8.
Altschul et al., "Basic Local Alignment Search Tool," J. Mol. Biol. 215:403-410, (1990).
Altschul, et al., "Gapped Blast and PSI-Blast; A New Generation of Protein Database Search Programs", Nucleic Acids Research, 25(17):3389-3402 (1997).
Argast et al., I-Ppol and I-Crel homing site sequence degeneracy determined by random mutagenesis and sequential in vitro enrichment, J. Mol. Biol., 1998, pp. 345-353, vol. 280.
Arnould, "Engineering of Large Numbers of Highly Specific Homing Endonucleases that Induce Recombination on Novel DNA Targets", J. Mol. Biol., 355:443-458 (2006).
Arnould, et al., "Engineered I-Crel Derivatives Cleaving Sequences from the Human XPC Gene can Induce Highly Efficient Gene Correction in Mammalian Cells", J. Mol. Biol., 371:49-65 (2007).
Aurora, et al., "Helix Capping", Protein Science, 7:21-38 (1998).
Ausubel, et al., Current Protocols in Molecular Biology, Wiley, 19996-Volume Loose Leaf Set; Do Not Cite Per Andrej.
Banerji, et al., "A Lymphocyte-Specific Cellular Enhancer is Loacated Downstream of the Joining Region in Immunoglobulin Heavy Chain Genes", Cell, 33:729-740 (1983).
Bibikova et al., Stimulation of homologous recombination through targeted cleavage by chimeric nucleases, Molecular and Cellular Biology, Jan. 2001, pp. 289-297, vol. 21 No. 1.

BMERC, "The PSA Protein Structure Prediction Server", http://bmerc-www/bi/edu/psa/, downloaded Mar. 3, 2011 (3 pages).
Brodelius, et al., "Fusion of Farnesyldiphosphate Synthase and epi-aristolochene Synthase, a Sesquiterpene Cyclase Involved in Capsidiol Biosynthesis in Nicotiana Tabacum", Eur. J. Biochem., 269:3570-3577 (2002).
Byrne, et al., "Multiplex Gene Regulation: A Two-Tiered Approach to Transgene Regulation in Transgenic Mice", Proc. Natl. Acad. Sci. USA, 86:5473-5477 (1989).
Cahill, et al., "Mechanisms of Eukaryotic DNA Double Strand Break Repair", Frontiers in Bioscience, 11:1958-1976 (2006).
Calame, et al., "Transcriptional Controlling Elements in the Immunoglobulin and T Cell Receptor Loci", Advances in Immunology, 43:235-275 (1988).
Camper, et al., "Postnatal Repression of the Alpha-Fetoprotein Gene is Enhancer Indepentent", Genes & Development, 3:537-546 (1989).
Cellectis Press Communication of Genome Modification Technology. Sep. 1, 2009. 1 page.
Chames, et al., "In vivo Selection of Engineered Homing Endonucleases using Double-Strand Break Induced Homologous Recombination", Nucleic Acids Research, vol. 33, No. 20 (2005) (10 pages).
Chevalier et al., The homing endonuclease I-Crel uses three metals, one of which is shared between the two active sites, Nature Structural Biology, Apr. 2001, pp. 312-316, vol. 8 No. 4.
Chevalier, et al., "Design, Activity, and Structure of a Highly Specific Artificial Endonuclease", Molecular Cell, 10:895-905 (2002).
Chevalier, et al., "Homing Endonucleases: Structural and Functional Insight into the Catalysts of Intron/Intein Mobility", Nucleic Acids Research, 29(18):3757-3774 (2001).
Chevalier, et al., "Metal-Dependent DNA Cleavage Mechanism of the I-Crel LAGLIDADG Homing Endonuclease", Biochemistry, 43:14015-14026 (2004).
Chilton, et al., "Targeted Integration of T-DNA into the Tobacco Genome at Double-Stranded Breaks: New Insignts on the Mechanism of T-DNA Integration", Plant Pyhsiology, 133:956-965 (2003).
Clapp, "Somatic Gene Therapy into Hematopoietic Cells: Curent Status and Future Implications", Current Controversies in Perinatal Care II, 20(1):155-168 (1993) (16 pages).
Communication from the European Patent Office for ongoing Opposition for European Application No. 03744485.8 on Apr. 14, 2010. 4 pages.
Communication from the European Patent Office for ongoing Opposition for European Application No. 03744485.8 regarding Decision of the Opposition Division on Jan. 26, 2010. 2 pages.
Communication from the European Patent Office for ongoing Opposition for European Application No. 03744485.8 regarding Interlocutory Decision in Opposition on Feb. 8, 2010. 114 pages.
Communication from the European Patent Office for ongoing Opposition for European Application No. 03744485.8 regarding Minutes of the Oral Proceedings on Nov. 18, 2009. 81 pages.
Communication from the European Patent Office for ongoing Opposition for European Patent Application No. 03744485.8 regarding Brief Communication dated Oct. 1, 2009. 1 page.
Communication from the European Patent Office for ongoing Opposition for European Patent Application No. 03744485.8 regarding Brief Communication dated Oct. 7, 2009. 1 page.
Communication from the European Patent Office in ongoing Opposition for European Patent Application No. 03744485.8 regarding Summons to Oral Proceedings dated Jun. 30, 2009. 9 pages.
Communication from the European Patent Office transmitting Third Part Observations for European Patent Application No. 03744485.8 dated Nov. 5, 2009. 8 pages.
Communication of Notices of Opposition from the European Patent Office in ongoing Opposition for European Patent Application No. 03744485.8 dated Jul. 10, 2008. 1 page.
Cozzone, Alain J. "Proteins: Fundamental Chemical Properties." Encyclopedia of Life Sciences. No month listed—2002. John Wiley & Sons Ltd. pp. 1-10.
Curiel, et al., "Adenovirus Enhancement of Transferrin-Polylysine-Mediated Gene Delivery", Proc. Natl. Acad. Sci. USA, 88:8850-8854 (1991).

(56) References Cited

OTHER PUBLICATIONS

Curiel, et al., "High-Efficiency Gene Transfer Mediated by Adenovirus Coupled to DNA-Polylysine Complexes", Human Gene Therapy, 3:147-154 (1992).
Dalgaard, Jacob Z. et al. "A Site-Specific Endonuclease Encoded by a Typical Archaeal Intron." Proc. Natl. Acad. Sci. Jun. 1993. vol. 90. pp. 5414-5417.
Duan et al., Crystal structure of PI-SceI, a homing endonuclease with protein splicing activity. Cell, May 16, 1997, vol. 89, pp. 555-564.
Edlund, et al., "Cell-Specific Expression of the Rat Insulin Gene: Evidence for Role of Two Distinct 5' Flanking Elements", Science, 230:912-916 (1985).
Eglitis, et al., "Retroviral Vectors for Introduction of Genes into Mammalian Cells", Biotechniques, 6(7):608-614 (1988) (8 pages).
Eglitis, et al., "Retroviral-Mediated Gene Transfer Into Hemopoietic Cells" Molecular Biology of Hemopoiesis, Plenum Press, New York, pp. 19-27 (1987) (11 pages).
Epinat, et al., "A Novel Engineered Meganuclease Induces Homologous Recombination in Yeast and Mammalian Cells", Nucleic Acids Research, 31(11):2952-2962 (2003).
Example: Generation of I-CreI Single Chain Molecules Based on Engineered Meganucleases. Cited in ongoing Opposition for European Patent Application No. 03744485.8 on Sep. 22, 2009. 4 pages.
Fajardo-Sanchez, et al., "Computer Design of Obligate Heterodimer Meganucleases Allows Efficient Cutting of Custom DNA Sequences", Nucleic Acids Research, 36(7):2163-2173 (2008).
Fersht Structure and Mechanism in Protein Science: A Guide to Enzyme Catalysis and Protein Folding, WH Freeman and Company, New York, (1999) (17 pages).
Filing by Opponent in ongoing Opposition for European Application No. 03744.485.8 dated Jan. 3, 2011. 28 pages.
Filing by Opponent in ongoing Opposition for European Application No. 03744485.8 dated Jun. 17, 2010. 10 pages.
Filing by Proprietor in ongoing Opposition for European Application No. 03744485.5 dated Dec. 30, 2010. 22 pages.
Filing by Proprietor in ongoing Opposition for European Patent Application No. 03744485.8 dated Jan. 16, 2009. 35 pages.
Filing by Proprietor in ongoing Opposition for European Patent Application No. 03744485.8 dated Sep. 22, 2009. 33 pages.
First Declaration of Derek Jantz cited in ongoing Opposition for European Patent Application No. 03744485.8. Jun. 4, 2008. 10 pages.
Fromm, et al., "Expression of Genes Transferred into Monocot and Dicot Plant Cells by Electroporation", Proc. Natl. Acad. Sci. USA, 82:5824-5828 (1985).
Fynan, et al., "DNA Vaccines: Protective Immunizations by Parenteral, Mucosal, and Gene-Gun Inoculations", Proc. Natl. Acad. Sci. USA, 90:11478-11482 (1993).
Generation of DmoCre Proteins with Flexible Linkers. Cited in ongoing Opposition for European Patent Application No. 03744485.8 on Dec. 30, 2010. 2 pages.
Gish, et al., "Identification of Protein Coding Regions by Database Similarity Search", Nature Genetics, 3:266-272 (1993).
Gossler, et al., "Transgenesis by Means of Blastocyst-Derived Embryonic Stem Cell Lines", Proc. Natl. Acad. Sci. USA, Developmental Biology, 83:9065-9069 (1986).
Gouble, et al., "Efficient in toto Targeted Recombination in Mouse Liver by Meganuclease-Induced Double-Strand Break", The Journal of Gene Medicine, 8:616-622 (2006).
Graham, et al., "Transformation of Rat Cells by DNA of Human Adenovirus 5", Virology, 54:536-539 (1973).
Gremillon, et al., "New Plant Growth-Modifying Properties of the Agrobacterium T-6b Oncogene Revealed by the use of a Dexamethasone-inducible Promoter", The Plant Journal, 37:218-228 (2004).
Grizot et al., Efficient Targeting of a SCID gene by an engineered single-chain homing endonuclease. Nucleic Acids Res. Sep. 2009;37(16):5405-19. doi: 10.1093/nar/gkp548. Epub Jul. 7, 2009.
Heath, Patrick J. et al. "The Structure of I-CreI, A Group I Intron-encoded Homing Endonuclease." Nature Structural Biology. vol. 4, No. 6. Jun. 1997. pp. 468-476.
Hu et al. "Probing the Structure of the PI-SeeI-DNA Complex by Affinity Cleavage and Affinity Photcross-linking." The Journal of Biological Chemistry. Jan. 28, 2000. vol. 275, No. 4. pp. 2705-2712.
Hudecz, et al., "Medium-Sized Peptides as Built in Carriers for Biologically Active Compounds", Medicinal Research Reviews, 25(6):679-736 (2005).
Ichiyanagi et al., Crystal structure of an archaeal intein-encoded homing endonuclease PI-PfuI, J. Mol. Biol., 2000, pp. 889-901, vol. 300.
Jacquier et al., An intron-encoded protein is active in a gene conversion process that spreads an intron into a mitochondrial gene. Cell, 1985, 41, 383-394.
Johnston, et al., "Chapter 17: Gene Gun Transfection of Animal Cells and Genetic Immunization", Methods in Cell Biology, vol. 43, Academic Press, Inc., pp. 353-365 (1994).
Jurica, et al., "DNA Recognition and Cleavage by the LAGLIDADG Homing Endonuclease I-CreI", Molecular Cell, 2:469-476 (1998).
Jurica, M.S. et al. "Homing Endonucleases: Structure, Function and Evolution." CMLS: Cellular and Molecular Life Sciences. Feb. 1999. vol. 55. pp. 1304-1326.
Kessel, et al., "Murine Developmental Control Genes", Science, 249:374-379 (1990).
Kim, et al., "Hybrid Restriction Enzymes: Zinc Finger Fusions to Fok I Cleavage Domain", Proc. Natl. Acad. Sci. USA, 93:1156-1160 (1996).
Korman, et al., "Expression of Human Class II Major Histocompatibility Complex Antigens using Retrovirus Vectors", Proc. Natl. Acad. Sci. USA, 84:2150-2154 (1987).
Lasic, et al., "Liposomes Revisited", Science, 267:1276-1276 (1995).
Li et al., Generation of single-chain LAGLIDADG homing endonucleases from native homodimeric precursor proteins. Nucleic Acids Res. Apr. 2009;37(5):1650-62. doi: 10.1093/nar/gkp004. Epub Jan. 19, 2009.
Liang et al. "Genetic Fusion of Subunits of a Dimeric Protein Substantially Enhances its Stability and Rate of Folding." Proc. Natl. Acad. Sci. vol. 90. Aug. 1993. pp. 7010-7014.
Lu, et al., "High Efficiency Retroviral Mediated Gene Transduction into Single Isolated Immature and Replatable DC34.sup.3+ Hematopoietic Stem/Progenitor Cells from Human Umbilical Cord Blood", J. Exp. Med, 178:2089-2096 (1993).
Lucas et al., Rapid evolution of the DNA-binding site in LAGLIDADG homing endonucleases, Nucleic Acids Research, 2001, pp. 960-969, vol. 29 No. 4.
Mack, et al., "A Small Bispecific Antibody Construct Expressed as a Functional Single-Chain Molecule with High Tumor Cell Cytotoxicity", Proc. Natl. Acad. Sci. USA, 92:7021-7025 (1995).
Madden, et al., "Applications of Network BLAST Server", Methods in Enzymology, 266:131-141 (1996).
McDaniel, et al., "Advances in Synthetic Biology: On the Path from Prototypes to Applications", Current Opinions in Biotechnology, 16:476-483 (2005).
Monnat, et al., "Generation of Highly Site-Specific DNA Double-Strand Breaks in Human Cells by the Homing Endonucleases I-PpoI and I-CreI", Biochemical and Biophysical Research Communications, 255:88-93 (1999).
Moure et al., Crystal structure of the intein homing endonuclease PI-SceI bound to its recognition sequence, Nature Structural Biology, Oct. 2002, pp. 764-770, vol. 9 No. 10.
New Example of DmoCre Meganuclease Cleaving RGI.10.2D34 DNA Target. Cited in ongoing Opposition for European Patent Application No. 03744485.8 on Jan. 16, 2009. 6 pages.
New Example of Single Chain Meganuclease Cleaving the RAGI Gene. Cited in ongoing Opposition for European Patent Application No. 03744485.8 on Jan. 16, 2009. 6 pages.
New Example of Single Chain Meganuclease Cleaving XPC Gene. Cited in ongoing Opposition for European Patent Application No. 03744485.8 on Jan. 16, 2009. 8 pages.
Notice of Appeal filing by Opponent in ongoing Opposition for European Application No. 03744485.8 dated Apr. 7, 2010. 4 pages.

(56) References Cited

OTHER PUBLICATIONS

Notice of Appeal filing by Proprietor in ongoing Opposition for European Application No. 03744485.8 dated Apr. 9, 2010. 2 pages.
Notice of Opposition filing by Opponent from the European Patent Office in ongoing Opposition for European Patent Application No. 03744485.8 dated Jun. 5, 2008. 33 pages.
Notice of Opposition filing by Proprietor in ongoing Opposition for European Patent Application No. 03744485.8 dated Nov. 3, 2008. 2 pages.
Omirulleh, et al., "Activity of a Chimeric Promoter with the Double CaMV 35S Enhancer Element in Protoplast-Derived Cells and Transgenic Plants in Maize", Plant Molecular Biology, 21:415-428 (1993).
Opposition Procedure filing by Proprietor in ongoing Opposition for European Patent Application No. 03744485.8 dated Nov. 17, 2009. 3 pages.
Pace, C. Nick et al. "Protein Stability." Encyclopedia of Life Sciences. No month listed—2001. John Wiley & Sons Ltd. pp. 1-4.
Papworth, et al, "Designer Zind-Finger Proteins and their Applications", Gene 366:27-38 (2006).
Perrin, M. Arnaud., Presentation on Jul. 7, 1994. 23 pages.
Pfeiffer, et al., "Lipoplex Gene Transfer of Inducible Nitric Oxide Synthases Inhibits the Reactive Intimal Hyperplasia After Expanded Polytetrafluoroethylene Bypass Grafting", Journal of Vascular Surgery, 43(5):1021-1027 (2006).
Pinkert, et al., "An Albumin Enhancer Located 10 kb Upstream Functions along with its Promoter to Direct Efficieint, Liver-Specific Expression in Transgenic Mice", Genes & Development, 1:268-276 (1987).
Poland, Bradley W. et al. "Structural Insights into the Protein Splicing Mechanism of PI-Scel." The Journal of Biological Chemistry. Jun. 2000. vol. 275, No. 22. pp. 16408-16413.
Porteus, et al., "Gene Targeting Using Zinc Finger Nucleases", Nature Biotechnology, 23(8):967-973 (2005).
Prieto, et al., "The C-terminal Loop of the Homing Endonuclease I-Crel is Essential for Site Recognition, DNA Binding and Cleavage", Nucleic Acids Research, 35(10):3262-3271 (2007).
Puchta, et al., "Two Different but Related Mechanisms are Used in Plants for the Repair of Genomic Double-Strand Breaks by Homologous Recombination", Proc. Natl. Acad. Sci. USA, 93:5055-5060 (1996).
Queen, et al., "Immunoglobulin Gene Transcription Is Activated by Downstream Sequence Elements", Cell, 33:741-748 (1983).
Rong, et al, "Targeted Mutagenesis by Homologous Recombination of D. Melanogaster", Genes and Development, 16:1568-1581 (2002) (15 pages).
Rosen, et al., "Homing Endonuclease I-Crel Derivatives with Novel DNA Target Specificities", Nucleic Acids Research, 34(17):4791-4800 (2006).
Rouet, et al., "Introduction of Double-Strand Breaks into the Genome of Mouse Cells by Expression of a Rare-Cutting Endonuclease", Molecular and Cellular Biology, 14(12):8096-8106 (1994).
Rui, et al., "Transfer of Anti-TFAR19 Monoclonal Antibody into HeLa Cells by in situ Electroporation Can Inhibit the Apoptosis", Life Sciences, 71:1771-1778 (2002).
Sali et al. "Comparative Protein Modelling by Satisfaction of Spatial Restraints." J. Mol. Biol. Jul. 1993. pp. 779-815.
Salomon, et al., "Capture of Genomic and T-DNA Sequences During Double-Strand Break Repair in Somatic Plant Cells", EMBO Journal, 17(20):6086-6095 (1998).
Sanger, et al., "DNA Sequencing with Chain-Terminating Inhibitors", Proc. Natl. Acad. Sci. USA, 74(12):5463-5468 (1977).
Second Declaration of Derek Jantz cited in ongoing Opposition for European Patent Application No. 03744485.8. Sep. 18, 2009. 51 pages.
Seligman et al., Genetic Analysis of the Chlamydomonas reinhardtii I-Crel mobile intron homing system in *Escherichia coli*, Genetics, Dec. 1997, pp. 1653-1664, vol. 147.
Seligman, et al., "Mutations Altering the Cleavage Specificity of a Homing Endonuclease", Nucleic Acids Research, 30(17):3870-3879 (2002).
Silva et al., Crystal structure of the thermostable archaeal intron-encoded endonuclease I-Dmol, J. Mol. Biol., 1999, pp. 1123-1136, vol. 286.
Silva, George H. et al. "From Monomeric to Homodimeric Endonucleases and Back: Engineering Novel Specificity of LAGLIDADG Enzymes." J. Mol. Biol. Jul. 2006. pp. 744-754.
Singh, et al., "Isolation and Characterization of a Flowering Plant Male Gametic Cell-Specific Promoter", FEBS Letters, 542:47-52 (2003).
Smith, et al., "A Combinatorial Approach to Create Artificial Homing Endonucleases Cleaving Chosen Sequences", Nucleic Acids Research, vol. 34, No. 22 (2006) (12 pages).
Smith, et al., "Requirements for Double-Strand Cleavage by Chimeric Restriction Enzymes with Zinc Finger DNA-Recognition Domains", Nucleic Acids Research, 28(17):3361-3369 (2000).
Sourdive, David J.D. et al. L'association Francaise Contre les Myopathies et Cellectis Lancent un Programme de Chirurgle Genomique Pour Guerir Les Maladies Genetiques. Cited in ongoing Opposition for European Patent Application No. 03744485.8 onJan. 16, 2009. 3 pages.
Spiegel, et al., "The Structure of I-Ceul Homing Endonuclease: Evolving Asymmetric DNA Recognition from a Symmetric Protein Scaffold", Structure, 14:869-880 (2006).
Statement of Grounds of Appeal filing by Proprietor in ongoing Opposition for European Application No. 03744485.5 dated Jun. 10, 2010. 60 pages.
Stoddard, "Homing Endonuclease Structure and Function", Quarterly Reviews of Biophysics, 38:49-95 (2006).
Submission of Declaration by Derek Jantz by Opponent in ongoing Opposition for European Patent Application No. 03744485.8 dated Nov. 11, 2009. 10 pages.
Submission of List of References by Opponent in ongoing Opposition for Europen Patent Application No. 0374485.8 dated Nov. 16, 2009. 3 pages.
Sussman, et al., Isolation and Characterization of New Homing Endonuclease Specificities at Individual Target Site Positions, J. Mol. Biol., 342:31-41 (2004).
Third Declaration of Derek Jantz cited in ongoing Opposition for European Patent Application No. 03744485.8. Nov. 11, 2009. 9 pages.
Turmel, Monique et al. "Evolutionary Conserved and Functionally Important Residues in the I-Ceul Homing Endonuclease." Nucleic Acid Research. Apr. 1997. vol. 25, No. 13. pp. 2610-2619. 10 pages.
Tzfira, et al., "Towards Targeted Mutagenesis and Gene Replacement in Plants", Trends in Biotechnologh, 23(12):567-569 (2005).
Ueda, et al., "Cell-Growth Control by Monomeric Antigen: the Cell Surface Expression of Lysozyme-Specific Ig V-domains Fused to Truncated Epo Receptor", Journal of Immunological Methods, 241:159-170 (2000).
Urnov, et al., "Highly Efficient Endogenous Human Gene Correction Using Designed Zinc-Finger Nucleases", Nature, 435:646-651 (2005).
Van Der Giessen, et al., "Comparison of the 23S Ribosomal RNA Genes and the Spacer Region Between the 16S and 23S rRNA Genes of the Closely Related Mycobacterium avium and Mycobacterium paratuberculosis and the Fast-Growing Mycobacterium Pheli", Microbiology, 140:1103-1108 (1994).
Wagner, et al., "Coupling of Adenovirus to Transferrin-Polylysine/DNA Conmplexes Greatly Enhances Receptor-Mediated Gene Delivery and Expression of Transfected Genes", Proc. Natl. Acad. Sci., 89:6099-6103 (1992).
Werner, Erik et al. "High Resolution Crystal Structure of Domain I of the Saccharomyces cerevisiae Homing Endonuclease PI-Scel." Nucelic Acid Research. Jul. 2002. vol. 30, No. 18. pp. 3962-3971. 10 pages.
Wild-type Sequence of I-Crel. Cited in ongoing Opposition for European Patent Application No. 03744485.8 on Jan. 16, 2009. 1 page.

(56) References Cited

OTHER PUBLICATIONS

Winoto, et al., "A Novel, Inducible and T Cell-Specific Enhancer Located at the 3' End of the T Cell Receptor .alpha. Locus", EMBO Journal, 8(3):729-733 (1989).
Wong, et al., "Electric Field Mediated Gene Transfer", Biochemical and Biophysical Research Communications, 107(2):584-587 (1982).
Wright, et al., "High-Frequency Homologous Recombination in Plants Mediated by Zinc-Finger Nucleases", The Plant Journal, 44:693-705 (2005).
Yeast Activity Assay of the LAM1/LAM2 Meganuclease. Cited in ongoing Opposition for European Patent Application No. 03744485.8 on Jan. 16, 2009 and Sep. 22, 2009. 5 pages.
Young, et al., "Gene Therapy for Oral Cancer: Efficient Delivery of a 'Suicide Gene' to Murine Oral Cancer Cells in Physiological Milieu", CDA Journal, 33(12):967-971 (2005).
Zatloukal, et al., "Transferrinfection: A Highly Efficient Way to Express Gene Constructs in Eukaryotic Cells", Annals New York Academy of Sciences, pp. 136-153 (1992).
Zhang, et al., "A Greedy Algorithm for Aligning DNA Sequences", Journal of Computational Biology, 7(1/2):203-214 (2000) (28 pages).

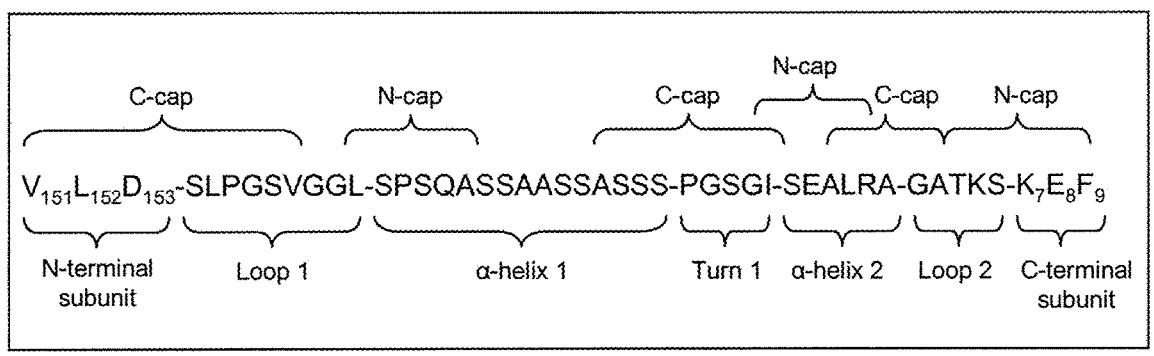
Structural Components of Linker 9

RATIONALLY-DESIGNED SINGLE-CHAIN MEGANUCLEASES WITH NON-PALINDROMIC RECOGNITION SEQUENCES

CROSS-REFERENCE TO RELATED APPLICATIONS

This application is a continuation of U.S. patent application Ser. No. 17/079,377, filed Oct. 23, 2020, which is a continuation of U.S. patent application Ser. No. 16/025,747, filed Jul. 2, 2018, which is a continuation of U.S. patent application Ser. No. 15/132,941, filed Apr. 19, 2016, now U.S. Pat. No. 10,041,053, which is a continuation of U.S. patent application Ser. No. 14/858,986, filed Sep. 18, 2015, now, U.S. Pat. No. 9,340,777, which is a continuation of U.S. patent application Ser. No. 14/723,840, filed May 28, 2015, which is a continuation of U.S. patent application Ser. No. 13/897,923, filed May 20, 2013, which is a continuation of U.S. patent application Ser. No. 12/771,163, filed Apr. 30, 2010, now U.S. Pat. No. 8,445,251, which is a continuation of U.S. International Patent Application PCT/US2008/082072, filed Oct. 31, 2008, which claims the benefit of U.S. Provisional Application No. 61/001,247, filed Oct. 31, 2007, the entire disclosures of which are incorporated by reference herein.

SEQUENCE LISTING

The instant application contains a Sequence Listing which has been submitted in XML ST.26 format via USPTO Patent Center and is hereby incorporated by reference in its entirety. Said XML ST.26 copy, created on Sep. 15, 2023 is named "P89339_1290USC9_ST.26_SeqList.xml" and is 116,181 bytes in size.

FIELD OF THE INVENTION

The invention relates to the field of molecular biology and recombinant nucleic acid technology. In particular, the invention relates to rationally-designed, non-naturally-occurring meganucleases in which a pair of enzyme subunits having specificity for different recognition sequence half-sites are joined into a single polypeptide to form a functional heterodimer with a non-palindromic recognition sequence. The invention also relates to methods of producing such meganucleases, and methods of producing recombinant nucleic acids and organisms using such meganucleases.

BACKGROUND OF THE INVENTION

Genome engineering requires the ability to insert, delete, substitute and otherwise manipulate specific genetic sequences within a genome, and has numerous therapeutic and biotechnological applications. The development of effective means for genome modification remains a major goal in gene therapy, agrotechnology, and synthetic biology (Porteus et al. (2005), *Nat. Biotechnol.* 23:967-73; Tzfira et al. (2005), *Trends Biotechnol.* 23:567-9; McDaniel et al. (2005), *Curr. Opin. Biotechnol.* 16:476-83). A common method for inserting or modifying a DNA sequence involves introducing a transgenic DNA sequence flanked by sequences homologous to the genomic target and selecting or screening for a successful homologous recombination event. Recombination with the transgenic DNA occurs rarely but can be stimulated by a double-stranded break in the genomic DNA at the target site. Numerous methods have been employed to create DNA double-stranded breaks, including irradiation and chemical treatments. Although these methods efficiently stimulate recombination, the double-stranded breaks are randomly dispersed in the genome, which can be highly mutagenic and toxic. At present, the inability to target gene modifications to unique sites within a chromosomal background is a major impediment to successful genome engineering.

One approach to achieving this goal is stimulating homologous recombination at a double-stranded break in a target locus using a nuclease with specificity for a sequence that is sufficiently large to be present at only a single site within the genome (see, e.g., Porteus et al. (2005), *Nat. Biotechnol.* 23:967-73). The effectiveness of this strategy has been demonstrated in a variety of organisms using chimeric fusions between an engineered zinc finger DNA-binding domain and the non-specific nuclease domain of the FokI restriction enzyme (Porteus (2006), *Mol. Ther.* 13:438-46; Wright et al. (2005), *Plant J.* 44:693-705; Urnov et al. (2005), *Nature* 435:646-51). Although these artificial zinc finger nucleases stimulate site-specific recombination, they retain residual non-specific cleavage activity resulting from under-regulation of the nuclease domain and frequently cleave at unintended sites (Smith et al. (2000), *Nucleic Acids Res.* 28:3361-9). Such unintended cleavage can cause mutations and toxicity in the treated organism (Porteus et al. (2005), *Nat. Biotechnol.* 23:967-73).

A group of naturally-occurring nucleases which recognize 15-40 base-pair cleavage sites commonly found in the genomes of plants and fungi may provide a less toxic genome engineering alternative. Such "meganucleases" or "homing endonucleases" are frequently associated with parasitic DNA elements such as group I self-splicing introns and inteins. They naturally promote homologous recombination or gene insertion at specific locations in the host genome by producing a double-stranded break in the chromosome, which recruits the cellular DNA-repair machinery (Stoddard (2006), *Q. Rv. Biophys.* 38:49-95). Meganucleases are commonly grouped into four families: the LAGLIDADG (SEQ ID NO: 55) family, the GIY-YIG family, the His-Cys box family and the HNH family. These families are characterized by structural motifs, which affect catalytic activity and recognition sequence. For instance, members of the LAGLIDADG (SEQ ID NO: 55) family are characterized by having either one or two copies of the conserved LAGLIDADG (SEQ ID NO: 55) motif (see Chevalier et al. (2001), *Nucleic Acids Res.* 29 (18): 3757-3774). The LAGLIDADG (SEQ ID NO: 55) meganucleases with a single copy of the LAGLIDADG (SEQ ID NO: 55) motif ("mono-LAGLIDADG (SESQ ID NO: 55) meganucleases") form homodimers, whereas members with two copies of the LAGLIDADG (SEQ ID NO: 55) motif ("di-LAGLIDADG (SEQ ID NO: 55) meganucleases") are found as monomers. Mono-LAGLIDADG (SEQ ID NO: 55) meganucleases such as I-CreI, I-CeuI, and IMsoI recognize and cleave DNA sites that are palindromic or pseudo-palindromic, while di-LAGLIDADG (SEQ ID NO:55) meganucleases such as I-SceI, I-AniI, and I-DmoI generally recognize DNA sites that are non-palindromic (Stoddard (2006), *Q. Rev. Biophys.* 38:49-95).

Natural meganucleases from the LAGLIDADG (SEQ ID NO: 55) family have been used to effectively promote site-specific genome modification in plants, yeast, *Drosophila*, mammalian cells and mice, but this approach has been limited to the modification of either homologous genes that conserve the megeanuclease recognition sequence (Monnat et al. (1999), *Biochem. Biophys. Res. Commun.* 255:88-93)

or to pre-engineered genomes into which a recognition sequence has been introduced (Rouet et al. (1994), *Mol. Cell. Biol.* 14:8096-106; Chilton et al. (2003), *Plant Physiol.* 133:956-65; Puchta et al. (1996), *Proc. Natl. Acad. Sci. USA* 93:5055-60; Rong et al. (2002), *Genes Dev.* 16:1568-81; Gouble et al. (2006), *J. Gene Med.* 8 (5): 616-622).

Systematic implementation of nuclease-stimulated gene modification requires the use of genetically engineered enzymes with customized specificities to target DNA breaks to existing sites in a genome and, therefore, there has been great interest in adapting meganucleases to promote gene modifications at medically or biotechnologically relevant sites (Porteus et al. (2005), *Nat. Biotechnol.* 23:967-73; Sussman et al. (2004), *J. Mol. Biol.* 342:31-41; Epinat et al. (2003), *Nucleic Acids Res.* 31:2952-62).

I-CreI is a member of the LAGLIDADG (SEQ ID NO: 55) family which recognizes and cuts a 22 base-pair recognition sequence in the chloroplast chromosome, and which presents an attractive target for meganuclease redesign. The wild-type enzyme is a homodimer in which each monomer makes direct contacts with 9 base pairs in the full-length recognition sequence. Genetic selection techniques have been used to modify the wild-type I-CreI cleavage site preference (Sussman et al. (2004), *J. Mol. Biol.* 342:31-41; Chames et al. (2005), *Nucleic Acids Res.* 33: e178; Seligman et al. (2002), *Nucleic Acids Res.* 30:3870-9, Arnould et al. (2006), *J. Mol. Biol.* 355:443-58, Rosen et al. (2006), *Nucleic Acids Res.* 34:4791-4800, Arnould et al. (2007). *J. Mol. Biol.* 371:49-65, WO 2008/010009, WO 2007/093918, WO 2007/093836, WO 2006/097784, WO 2008/059317, WO 2008/059382, WO 2008/102198, WO 2007/060495, WO 2007/049156, WO 2006/097853, WO 2004/067736). More recently, a method of rationally-designing mono-LAGLIDADG (SEQ ID NO: 55) meganucleases was described which is capable of comprehensively redesigning I-CreI and other such meganucleases to target widely-divergent DNA sites, including sites in mammalian, yeast, plant, bacterial, and viral genomes (WO 2007/047859).

A major limitation of using mono-LAGLIDADG (SEQ ID NO: 55) meganucleases such as I-CreI for most genetic engineering applications is the fact that these enzymes naturally target palindromic DNA recognition sites. Such lengthy (10-40 bp) palindromic DNA sites are rare in nature and are unlikely to occur by chance in a DNA site of interest. In order to target a non-palindromic DNA site with a mono-LAGLIDADG (SEQ ID NO: 55) meganuclease, one can produce a pair of monomers which recognize the two different half-sites and which heterodimerize to form a meganuclease that cleaves the desired non-palindromic site. Heterodimerization can be achieved either by co-expressing a pair of meganuclease monomers in a host cell or by mixing a pair of purified homodimeric meganucleases in vitro and allowing the subunits to re-associate into heterodimers (Smith et al. (2006), *Nuc. Acids Res.* 34:149-157; Chames et al. (2005), *Nucleic Acids Res.* 33:178-186; WO 2007/047859, WO 2006/097854, WO 2007/057781, WO 2007/049095, WO 2007/034262). Both approaches suffer from two primary limitations: (1) they require the expression of two meganuclease genes to produce the desired heterodimeric species (which complicates gene delivery and in vivo applications) and (2) the result is a mixture of approximately 25% the first homodimer, 50% the heterodimer, and 25% the second homodimer, whereas only the heterodimer is desired. This latter limitation can be overcome to a large extent by genetically engineering the dimerization interfaces of the two meganucleases to promote heterodimerization over homodimerization as described in WO 2007/047859, WO 2008/093249, WO 2008/093152, and Fajardo-Sanchez et al. (2008). *Nucleic Acids Res.* 36:2163-2173. Even so, two meganuclease genes must be expressed and homodimerization is not entirely prevented.

An alternative approach to the formation of meganucleases with non-palindromic recognition sites derived from one or more mono-LAGLIDADG (SEQ_ID NO: 55) meganucleases is the production of a single polypeptide which comprises a fusion of the LAGLIDADG (SEQ ID NO: 55) subunits derived from two meganucleases. Two general methods can be applied to produce such a meganuclease.

In the first method, one of the two LAGLIDADG (SEQ ID NO: 55) subunits of a di-LAGLIDADG (SEQ ID NO: 55) meganuclease can be replaced by a LAGLIDADG (SEQ ID NO: 55) subunit from a mono-LAGLIDADG (SEQ ID NO: 55) meganuclease. This approach was demonstrated by replacing the C-terminal subunit of the di-LAGLIDADG (SEQ ID NO: 55) I-DmoI meganuclease with an I-CreI subunit (Epinat et al. (2003), *Nucleic Acids Res.* 31:2952-62; Chevalier et al. (2002), *Mol. Cell* 10:895-905; WO 2003/078619). The result was a hybrid I-DmoI/I-CreI meganuclease which recognized and cleaved a hybrid DNA site.

In the second method, a pair of mono-LAGLIDADG (SEQ ID NO: 55) subunits can be joined by a peptide linker to create a "single-chain heterodimer meganuclease." One attempt to produce such a single-chain derivative of I-CreI has been reported (Epinat et al. (2003), *Nucleic Acids Res.* 31:2952-62; WO 2003/078619). However, as discussed herein as well as in Fajardo-Sanchez et al. (2008), *Nucleic Acids Res.* 36:2163-2173, there is now evidence suggesting that this method did not produce a single-chain heterodimer meganuclease in which the covalently joined I-CreI subunits functioned together to recognize and cleave a non-palindromic recognition site.

Therefore, there remains a need in the art for methods for the production of single-chain heterodimer meganucleases derived from mono-LAGLIDADG (SEQ ID NO: 55) enzymes such as I-CreI to recognize and cut non-palindromic DNA sites.

SUMMARY OF THE INVENTION

The present invention is based, in part, upon the development of fusion proteins in which a peptide linker covalently joins two heterologous LAGLIDADG (SEQ ID NO: 55) meganuclease subunits to form a "single-chain heterodimer meganuclease" or "single-chain meganuclease", in which at least the N-terminal subunit is derived from a mono-LAGLIDADG (SEQ ID NO: 55) meganuclease, and in which the subunits function together to preferentially bind to and cleave a non-palindromic DNA recognition site which is a hybrid of the recognition half-sites of the two subunits. In particular, the invention can be used to genetically engineer single-chain meganucleases which recognize non-palindromic DNA sequences that naturally-occurring meganucleases do not recognize. The invention also provides methods that use such meganucleases to produce recombinant nucleic acids and organisms by utilizing the meganucleases to cause recombination of a desired genetic sequence at a limited number of loci within the genome of the organism for, inter alia, genetic engineering, gene therapy, treatment of pathogenic infections, and in vitro applications in diagnostics and research.

Thus, in some embodiments, the invention provides recombinant single-chain meganucleases comprising a pair of covalently joined LAGLIDADG (SEQ ID NO: 55) subunits derived from one or more mono-LAGLIDADG (SEQ ID NO: 55) meganucleases which function together to recognize and cleave a non-palindromic recognition site. In some embodiments, the mono-LAGLIDADG (SEQ ID NO: 55) subunit is derived from a wild-type meganuclease selected from I-CreI, I-MsoI and I-CeuI.

In other embodiments, the invention provides recombinant single-chain meganucleases comprising a pair of mono-LAGLIDADG (SEQ ID NO: 55) subunits in which the N-terminal subunit is derived from a wild-type meganuclease selected from I-CreI, I-MsoI and I-CeuI, and the C-terminal subunit is also derived from a wild-type meganuclease selected from I-CreI, I-MsoI and I-CeuI, but the N-terminal subunit is derived from a wild-type meganuclease of a different species than the C-terminal subunit.

In some embodiments, the invention provides recombinant single-chain meganucleases comprising a pair of LAGLIDADG (SEQ ID NO: 55) subunits in which the N-terminal subunit is derived from a wild-type meganuclease selected from I-CreI, I-MsoI and I-CeuI, and the C-terminal subunit is derived from a single LAGLIDADG (SEQ ID NO: 55) subunit from a wild-type di-LAGLIDADG (SEQ ID NO: 55) meganuclease selected from I-DmoI, I-SceI and I-AniI.

Wild-type mono-LAGLIDADG (SEQ ID NO: 55) meganucleases include, without limitation, the I-CreI meganuclease of SEQ ID NO: 1, the I-MsoI meganuclease of SEQ ID NO: 2, and the I-CeuI meganuclease of SEQ ID NO: 3. Wild-type di-LAGLIDADG (SEQ ID NO: 55) meganucleases include, without limitation, the I-DmoI meganuclease of SEQ ID NO: 4, the I-SceI meganuclease of SEQ ID NO: 5, and the I-AniI meganuclease of SEQ ID NO: 6.

Wild-type LAGLIDADG (SEQ ID NO: 55) domains include, without limitation, residues 9-151 of the wild-type I-CreI meganuclease of SEQ ID NO: 1; residues 11-162 of the wild-type I-MsoI meganuclease of SEQ ID NO: 2; and residues 55-210 of the wild-type I-CeuI meganuclease of SEQ ID NO: 3, residues 9-96 of the wild-type I-DmoI of SEQ ID NO: 4; residues 105-178 of the wild-type I-DmoI of SEQ ID NO: 4; residues 32-123 of the wild-type I-SceI of SEQ ID NO: 5; residues 134-225 of the wild-type I-SceI of SEQ ID NO: 5; residues 4-121 of the wild-type I-AniI of SEQ ID NO: 6; and residues 136-254 of the wild-type I-AniI of SEQ ID NO: 6.

LAGLIDADG (SEQ ID NO: 55) subunits derived from a wild-type LAGLIDADG (SEQ ID NO: 55) meganuclease include, without limitation, subunits including a LAGLIDADG (SEQ ID NO: 55) domain that has at least 85% sequence identity, or 85%-100% sequence identity, to any one of residues 9-151 of the wild-type I-CreI meganuclease of SEQ ID NO: 1; residues 11-162 of the wild-type I-MsoI meganuclease of SEQ ID NO: 2; and residues 55-210 of the wild-type I-CeuI meganuclease of SEQ ID NO: 3, residues 9-96 of the wild-type I-DmoI of SEQ ID NO: 4; residues 105-178 of the wild-type I-DmoI of SEQ ID NO: 4; residues 32-123 of the wild-type I-SceI of SEQ ID NO: 5; residues 134-225 of the wild-type I-SceI of SEQ ID NO: 5; residues 4-121 of the wild-type I-AniI of SEQ ID NO: 6; and residues 136-254 of the wild-type I-AniI of SEQ ID NO: 6.

LAGLIDADG (SEQ ID NO: 55) subunits derived from a wild-type LAGLIDADG (SEQ ID NO: 55) meganuclease also include, without limitation, subunits comprising any of the foregoing polypeptide sequences in which one or more amino acid modifications have been included according to the methods of rationally-designing LAGLIDADG (SEQ ID NO: 55) meganucleases disclosed in WO 2007/047859, as well as other non-naturally-occurring meganuclease variants known in the art.

In certain embodiments, the invention provides recombinant single-chain meganucleases comprising a pair of LAGLIDADG (SEQ ID NO: 55) subunits derived from naturally-occurring LAGLIDADG (SEQ ID NO: 55) subunits each of which recognizes a wild-type DNA half-site selected from GAAACTGTC; GACAGTTTC; CAAAACGTC; GACGTTTTG; CAGAACGTC; GACGTTCTG; GGAACTGTC; GACAGTTCC; ATAACGGTC; GACCGTTAT; TTCGCTACC; GGTAGCGAA; TAGGG; CCCTA; TAATGGGAC; GTCCCATTA; GCCGGAAC; GTTCCGGC; AACGGCC; GGCCGTT; TTTACAGA; TCTGTAAA; CTGAGGAGG; and CCTCCTCAG.

In other embodiments, the invention provides recombinant single-chain meganucleases comprising a pair of LAGLIDADG (SEQ ID NO: 55) subunits genetically engineered with respect to DNA-binding specificity, each of which recognizes a DNA half-site that differs by at least one base from a wild-type DNA half-site selected from GAAACTGTC; GACAGTTTC; CAAAACGTC; GACGTTTTG; CAGAACGTC; GACGTTCTG; GGAACTGTC; GACAGTTCC; ATAACGGTC; GACCGTTAT; TTCGCTACC; GGTAGCGAA; TAGGG; CCCTA; TAATGGGAC; GTCCCATTA; GCCGGAAC; GTTCCGGC; AACGGCC; GGCCGTT; TTTACAGA; TCTGTAAA; CTGAGGAGG; and CCTCCTCAG.

In other embodiments, the invention provides recombinant single-chain meganucleases comprising a pair of LAGLIDADG (SEQ ID NO: 55) subunits in which one subunit is natural and recognizes a wild-type DNA half-site selected GAAACTGTC; GACAGTTTC; CAAAACGTC; GACGTTTTG; CAGAACGTC; GACGTTCTG; GGAACTGTC; GACAGTTCC; ATAACGGTC; GACCGTTAT; TTCGCTACC; GGTAGCGAA; TAGGG; CCCTA; TAATGGGAC; GTCCCATTA; GCCGGAAC; GTTCCGGC; AACGGCC; GGCCGTT; TTTACAGA; TCTGTAAA; CTGAGGAGG; and CCTCCTCAG and the other is genetically engineered with respect to DNA-binding specificity and recognizes a DNA site that differs by at least one base from a wild-type DNA half-site selected from GAAACTGTC; GACAGTTTC; CAAAACGTC; GACGTTTTG; CAGAACGTC; GACGTTCTG; GGAACTGTC; GACAGTTCC; ATAACGGTC; GACCGTTAT; TTCGCTACC; GGTAGCGAA; TAGGG; CCCTA; TAATGGGAC; GTCCCATTA; GCCGGAAC; GTTCCGGC; AACGGCC; GGCCGTT; TTTACAGA; TCTGTAAA; CTGAGGAGG; and CCTCCTCAG.

In some embodiments, the polypeptide linker joining the LAGLIDADG (SEQ ID NO: 55) subunits is a flexible linker. In particular embodiments, the linker can include 15-40 residues, 25-31 residues, or any number within those ranges. In other particular embodiments, at least 50%, or 50%-100%, of the residues forming the linker are polar uncharged residues.

In other embodiments, the polypeptide linker joining the LAGLIDADG (SEQ ID NO: 55) subunits has a stable secondary structure. In particular embodiments, the stable secondary structure comprises at least two α-helix structures. In other particular embodiments, the stable secondary structure comprises from N-terminus to C-terminus a first loop, a first α-helix, a first turn, a second α-helix, and a second loop. In some particular embodiments, the linker can include 23-56 residues, or any number within that range.

In another aspect, the invention provides for various methods of use for the single-chain meganucleases described and enabled herein. These methods include producing genetically-modified cells and organisms, treating diseases by gene therapy, treating pathogen infections, and using the recombinant single-chain meganucleases for in vitro applications for diagnostics and research.

Thus, in one aspect, the invention provides methods for producing a genetically-modified eukaryotic cell including an exogenous sequence of interest inserted in a chromosome, by transfecting the cell with (i) a first nucleic acid sequence encoding a meganuclease of the invention, and (ii) a second nucleic acid sequence including said sequence of interest, wherein the meganuclease produces a cleavage site in the chromosome and the sequence of interest is inserted into the chromosome at the cleavage site either by homologous recombination or non-homologous end-joining.

Alternatively, in another aspect, the invention provides methods for producing a genetically-modified eukaryotic cell including an exogenous sequence of interest inserted in a chromosome, by introducing a meganuclease protein of the invention into the cell, and transfecting the cell with a nucleic acid including the sequence of interest, wherein the meganuclease produces a cleavage site in the chromosome and the sequence of interest is inserted into the chromosome at the cleavage site either by homologous recombination or non-homologous end-joining.

In another aspect, the invention provides methods for producing a genetically-modified eukaryotic cell by disrupting a target sequence in a chromosome, by transfecting the cell with a nucleic acid encoding a meganuclease of the invention, wherein the meganuclease produces a cleavage site in the chromosome and the target sequence is disrupted by non-homologous end-joining at the cleavage site.

In another aspect, the invention provides methods of producing a genetically-modified organism by producing a genetically-modified eukaryotic cell according to the methods described above, and growing the genetically-modified eukaryotic cell to produce the genetically-modified organism. In these embodiments, the eukaryotic cell can be selected from a gamete, a zygote, a blastocyst cell, an embryonic stem cell, and a protoplast cell.

In another aspect, the invention provides methods for treating a disease by gene therapy in a eukaryote, by transfecting at least one cell of the eukaryote with one or more nucleic acids including (i) a first nucleic acid sequence encoding a meganuclease of the invention, and (ii) a second nucleic acid sequence including a sequence of interest, wherein the meganuclease produces a cleavage site in the chromosome and the sequence of interest is inserted into the chromosome by homologous recombination or non-homologous end-joining, and insertion of the sequence of interest provides gene therapy for the disease.

Alternatively, in another aspect, the invention provides methods for treating a disease by gene therapy in a eukaryote, by introducing a meganuclease protein of the invention into at least one cell of the eukaryote, and transfecting the cell with a nucleic acid including a sequence of interest, wherein the meganuclease produces a cleavage site in the chromosome and the sequence of interest is inserted into the chromosome at the cleavage site by homologous recombination or non-homologous end-joining, and insertion of the sequence of interest provides gene therapy for the disease.

In another aspect, the invention provides methods for treating a disease by gene therapy in a eukaryote by disrupting a target sequence in a chromosome of the eukaryotic, by transfecting at least one cell of the eukaryote with a nucleic acid encoding a meganuclease of the invention, wherein the meganuclease produces a cleavage site in the chromosome and the target sequence is disrupted by non-homologous end-joining at the cleavage site, wherein disruption of the target sequence provides the gene therapy for the disease.

In another aspect, the invention provides methods for treating a viral or prokaryotic pathogen infection in a eukaryotic host by disrupting a target sequence in a genome of the pathogen, by transfecting at least one infected cell of the host with a nucleic acid encoding a meganuclease of the invention, wherein the meganuclease produces a cleavage site in the genome and the target sequence is disrupted by either (1) non-homologous end-joining at the cleavage site or (2) by homologous recombination with a second nucleic acid, and wherein disruption of the target sequence provides treatment for the infection.

These and other aspects and embodiments of the invention will be apparent to one of ordinary skill in the art based upon the following detailed description of the invention.

DETAILED DESCRIPTION OF THE INVENTION

FIG. 1 is a diagram of the structural components of one embodiment of a linker of the invention (Linker 9) and N-terminal and C-terminal residues of the endonuclease subunits joined by the linker (SEQ ID NO: 109).

DETAILED DESCRIPTION OF THE INVENTION

1.1 Introduction

The present invention is based, in part, upon the development of fusion proteins in which a peptide linker covalently joins two heterologous LAGLIDADG_(SEQ ID NO: 55) meganuclease subunits to form a "single-chain heterodimer meganuclease" in which the subunits function together to preferentially bind to and cleave a non-palindromic DNA recognition site which is a hybrid of the recognition half-sites of the two subunits. In particular, the invention can be used to genetically engineer single-chain meganucleases which recognize non-palindromic DNA sequences that naturally-occurring meganucleases do not recognize.

This discovery has been used, as is described in detail below, to join mono-LAGLIDADG (SEQ ID NO: 55) meganucleases, which naturally function as homodimers, into single-chain meganucleases. Further, the discovery has been used to join mono-LAGLIDADG (SEQ ID NO: 55) meganucleases which have been re-engineered with respect to DNA-recognition specificity into single-chain heterodimers which recognize and cleave DNA sequences that are a hybrid of the palindromic sites recognized by the two meganuclease homodimers. The invention provides exemplary peptide linker sequences for joining LAGLIDADG (SEQ ID NO: 55) subunits into single polypeptides. Importantly, the invention provides a general method for the production of linker sequences and the selection of fusion points for linking different LAGLIDADG (SEQ ID NO: 55) subunits to produce functional rationally-designed single-chain meganucleases.

The invention also provides methods that use such meganucleases to produce recombinant nucleic acids, cells and organisms by utilizing the meganucleases to cause recombination of a desired genetic sequence at a limited number of loci within the genome of the organism for, inter alia, genetic engineering, gene therapy, treatment of pathogenic infections and cancer, and in vitro applications in diagnostics and research.

As a general matter, the invention provides methods for generating single-chain meganucleases comprising two LAGLIDADG (SEQ ID NO: 55) subunits in which the N-terminal subunit is derived from a natural mono-LAGLIDADG (SEQ ID NO: 55) meganuclease such as I-CreI, I-MsoI, or I-CeuI or a variant thereof and the C-terminal subunit is derived from either a mono-LAGLIDADG (SEQ ID NO: 55) meganuclease or one of the two domains of a di-LAGLIDADG (SEQ ID NO: 55) meganuclease such as I-SceI, I-DmoI, or I-AniI. The method is distinct from those described previously (Epinat et al. (2003), *Nucleic Acids Res.* 31:2952-62; Chevalier et al. (2002), *Mol. Cell* 10:895-905; WO 2003/078619) in that it requires the use of specific and novel linker sequences and fusion points to produce recombinant single-chain meganucleases in which the N-terminal subunit is derived from a mono-LAGLIDADG (SEQ ID NO: 55) meganuclease.

As described in detail below, the method of producing a recombinant single-chain meganuclease includes the use of defined fusion points in the two LAGLIDADG (SEQ ID NO: 55) subunits to be joined as well as the use of defined linker sequences to join them into a single polypeptide. In addition, a set of rules is provided for identifying fusion points not explicitly described herein as well as for producing functional linker sequences that are not explicitly described herein.

Thus, in one aspect, the invention provides methods for producing recombinant single-chain LAGLIDADG (SEQ ID NO: 55) meganucleases. In another aspect, the invention provides the recombinant single-chain meganucleases resulting from these methods. In another aspect, the invention provides methods that use such single-chain meganucleases to produce recombinant nucleic acids, cells and organisms in which a desired DNA sequence or genetic locus within the genome of cell or organism is modified by the insertion, deletion, substitution or other manipulation of DNA sequences. In another aspect, the invention provides methods for reducing the survival of pathogens or cancer cells using single-chain meganucleases which have pathogen-specific or cancer-specific recognition sequences.

1.2 References and Definitions

The patent and scientific literature referred to herein establishes knowledge that is available to those of skill in the art. The issued U.S. patents, allowed applications, published U.S. and PCT international applications, and references, including GenBank database sequences, that are cited herein are hereby incorporated by reference to the same extent as if each was specifically and individually indicated to be incorporated by reference.

As used herein, the term "meganuclease" refers to an endonuclease that binds double-stranded DNA at a recognition sequence that is greater than 12 base pairs in length. Naturally-occurring meganucleases can be monomeric (e.g., I-SceI) or dimeric (e.g., I-CreI). The term meganuclease, as used herein, can be used to refer to monomeric meganucleases, dimeric meganucleases, to the monomers which associate to form a dimeric meganuclease, or to a recombinant single-chain meganuclease of the invention. The term "homing endonuclease" is synonymous with the term "meganuclease."

As used herein, the term "LAGLIDADG (SEQ ID NO: 55) meganuclease" refers either to meganucleases including a single LAGLIDADG (SEQ ID NO: 55) motif, which are naturally dimeric, or to meganucleases including two LAGLIDADG (SEQ ID NO: 55) motifs, which are naturally monomeric. The term "mono-LAGLIDADG (SEQ ID NO: 55) meganuclease" is used herein to refer to meganucleases including a single LAGLIDADG (SEQ ID NO: 55) motif, and the term "di-LAGLIDADG (SEQ ID NO: 55) meganuclease" is used herein to refer to meganucleases including two LAGLIDADG (SEQ ID NO: 55) motifs, when it is necessary to distinguish between the two. Each of the two structural domains of a di-LAGLIDADG (SEQ ID NO: 55) meganuclease which includes a LAGLIDADG (SEQ ID NO: 55) motif and has enzymatic activity, and each of the individual monomers of a mono-LAGLIDADG (SEQ ID NO: 55) meganuclease, can be referred to as a LAGLIDADG (SEQ ID NO: 55) subunit, or simply "subunit".

As used herein, and in reference to a peptide sequence, "end" refers to the C-terminus and "beginning" refers to the N-terminus. Thus, for example, "the beginning of the LAGLIDADG (SEQ ID NO: 55) motif" refers to the N-terminal-most amino acid in the peptide sequence comprising the LAGLIDADG (SEQ ID NO: 55) motif whereas "the end of the LAGLIDADG (SEQ ID NO: 55) motif" refers to the C-terminal-most amino acid in the peptide sequence comprising the LAGLIDADG (SEQ ID NO: 55) motif.

As used herein, the term "rationally-designed" means non-naturally-occurring and/or genetically engineered. The rationally-designed meganucleases of the invention differ from wild-type or naturally-occurring meganucleases in their amino acid sequence or primary structure, and may also differ in their secondary, tertiary or quaternary structure. In addition, the rationally-designed meganucleases of the invention also differ from wild-type or naturally-occurring meganucleases in recognition sequence-specificity and/or activity.

As used herein, with respect to a protein, the term "recombinant" means having an altered amino acid sequence as a result of the application of genetic engineering techniques to nucleic acids which encode the protein, and cells or organisms which express the protein. With respect to a nucleic acid, the term "recombinant" means having an altered nucleic acid sequence as a result of the application of genetic engineering techniques. Genetic engineering techniques include, but are not limited to, PCR and DNA cloning technologies; transfection, transformation and other gene transfer technologies; homologous recombination; site-directed mutagenesis; and gene fusion. In accordance with this definition, a protein having an amino acid sequence identical to a naturally-occurring protein, but produced by cloning and expression in a heterologous host, is not considered recombinant.

As used herein with respect to recombinant proteins, the term "modification" means any insertion, deletion or substitution of an amino acid residue in the recombinant sequence relative to a reference sequence (e.g., a wild-type).

As used herein, the term "genetically-modified" refers to a cell or organism in which, or in an ancestor of which, a genomic DNA sequence has been deliberately modified by recombinant technology. As used herein, the term "genetically-modified" encompasses the term "transgenic."

As used herein, the term "wild-type" refers to any naturally-occurring form of a meganuclease. The term "wild-type" is not intended to mean the most common allelic variant of the enzyme in nature but, rather, any allelic variant found in nature. Wild-type meganucleases are distinguished from recombinant or non-naturally-occurring meganucleases.

As used herein, the term "recognition sequence half-site" or simply "half site" means a nucleic acid sequence in a double-stranded DNA molecule which is recognized by a monomer of a mono-LAGLIDADG (SEQ ID NO: 55) meganuclease or by one LAGLIDADG (SEQ ID NO: 55) subunit of a di-LAGLIDADG (SEQ ID NO: 55) meganuclease.

As used herein, the term "recognition sequence" refers to a pair of half-sites which is bound and cleaved by either a mono-LAGLIDADG (SEQ ID NO: 55) meganuclease dimer or a di-LAGLIDADG (SEQ ID NO: 55) meganuclease monomer. The two half-sites may or may not be separated by base pairs that are not specifically recognized by the enzyme. In the cases of I-CreI, I-MsoI and I-CeuI, the recognition sequence half-site of each monomer spans 9 base pairs, and the two half-sites are separated by four base pairs which are not contacted directly by binding of the enzyme but which constitute the actual cleavage site (which has a 4 base pair overhang). Thus, the combined recognition sequences of the I-CreI, I-MsoI and I-CeuI meganuclease dimers normally span 22 base pairs, including two 9 base pair half-sites flanking a 4 base pair cleavage site. In the case of the I-SceI meganuclease, which is a di-LAGLIDADG (SEQ ID NO: 55) meganuclease monomer, the recognition sequence is an approximately 18 bp non-palindromic sequence, and there are no central base pairs which are not specifically recognized. By convention, one of the two strands is referred to as the "sense" strand and the other the "antisense" strand, although neither strand may encode protein.

As used herein, the term "specificity" means the ability of a meganuclease to recognize and cleave double-stranded DNA molecules only at a particular sequence of base pairs referred to as the recognition sequence, or only at a particular set of recognition sequences. The set of recognition sequences will share certain conserved positions or sequence motifs, but may be degenerate at one or more positions. A highly-specific meganuclease is capable of cleaving only one or a very few recognition sequences. Specificity can be determined in a cleavage assay as described in Example 1. As used herein, a meganuclease has "altered" specificity if it binds to and cleaves a recognition sequence which is not bound to and cleaved by a reference meganuclease (e.g., a wild-type) under physiological conditions, or if the rate of cleavage of a recognition sequence is increased or decreased by a biologically significant amount (e.g., at least 2×, or 2×-10×) relative to a reference meganuclease.

As used herein, the term "palindromic" refers to a recognition sequence consisting of inverted repeats of identical half-sites. However, the palindromic sequence need not be palindromic with respect to the central base pairs which are not directly contacted by binding of the enzyme (e.g., the four central base pairs of an I-CreI recognition site). In the case of naturally-occurring dimeric meganucleases, palindromic DNA sequences are recognized by homodimers in which the two monomers make contacts with identical half-sites.

As used herein, the term "pseudo-palindromic" refers to a recognition sequence consisting of inverted repeats of non-identical or imperfectly palindromic half-sites. In addition to central base pairs that are not directly contacted by binding of the enzyme, the pseudo-palindromic sequence can deviate from a palindromic sequence between the two recognition half-sites at 1-3 base pairs at each of the two half-sites. Pseudo-palindromic DNA sequences are typical of the natural DNA sites recognized by wild-type homodimeric meganucleases in which two identical enzyme monomers make contacts with slightly different half-sites.

As used herein, the term "non-palindromic" refers to a recognition sequence composed of two unrelated half-sites of a meganuclease. In this case, the non-palindromic sequence need not be palindromic with respect to either the central base pairs or 4 or more base pairs at each of the two half-sites. Non-palindromic DNA sequences are recognized by either di-LAGLIDADG (SEQ ID NO: 55) meganucleases, highly degenerate mono-LAGLIDADG (SEQ ID NO: 55) meganucleases (e.g., I-CeuI) or by heterodimers of mono-LAGLIDADG (SEQ ID NO: 55) meganuclease monomers that recognize non-identical half-sites. In the latter case, a non-palindromic recognition sequence may be referred to as a "hybrid sequence" because the heterodimer of two different mono-LAGLIDADG (SEQ ID NO: 55) monomers, whether or not they are fused into a single polypeptide, will cleave a recognition sequence comprising one half-site recognized by each monomer. Thus, the heterodimer recognition sequence is a hybrid of the two homodimer recognition sequences.

As used herein, the term "linker" refers to an exogenous peptide sequence used to join two LAGLIDADG (SEQ ID NO: 55) subunits into a single polypeptide. A linker may have a sequence that is found in natural proteins, or may be an artificial sequence that is not found in any natural protein. A linker may be flexible and lacking in secondary structure or may have a propensity to form a specific three-dimensional structure under physiological conditions.

As used herein, the term "fusion point" refers to the junction between a LAGLIDADG (SEQ ID NO: 55) subunit and a linker. Specifically, the "N-terminal fusion point" is the last (C-terminal-most) amino acid of the N-terminal LAGLIDADG (SEQ ID NO: 55) subunit prior to the linker sequence and the "C-terminal fusion point" is the first (N-terminal-most) amino acid of the C-terminal LAGLIDADG (SEQ ID NO: 55) subunit following the linker sequence.

As used herein, the term "single-chain meganuclease" refers to a polypeptide comprising a pair of LAGLIDADG (SEQ ID NO: 55) subunits joined by a linker. A single-chain meganuclease has the organization: N-terminal subunit-Linker-C-terminal subunit. A single-chain meganuclease is distinguished from a natural di-LAGLIDADG (SEQ ID NO: 55) meganuclease in that the N-terminal subunit must be derived from a mono-LAGLIDADG (SEQ ID NO: 55) meganuclease and, therefore, the linker must be exogenous to the N-terminal subunit.

As used herein, the term "homologous recombination" refers to the natural, cellular process in which a double-stranded DNA-break is repaired using a homologous DNA sequence as the repair template (see, e.g., Cahill et al. (2006), *Front. Biosci.* 11:1958-1976). The homologous DNA sequence may be an endogenous chromosomal sequence or an exogenous nucleic acid that was delivered to the cell. Thus, in some embodiments, a rationally-designed meganuclease is used to cleave a recognition sequence within a target sequence and an exogenous nucleic acid with homology to or substantial sequence similarity with the target sequence is delivered into the cell and used as a template for repair by homologous recombination. The DNA sequence of the exogenous nucleic acid, which may differ significantly from the target sequence, is thereby incorporated into the chromosomal sequence. The process of homologous recombination occurs primarily in eukaryotic organisms. The term "homology" is used herein as equivalent to "sequence similarity" and is not intended to require identity by descent or phylogenetic relatedness.

As used herein, the term "non-homologous end-joining" refers to the natural, cellular process in which a double-stranded DNA-break is repaired by the direct joining of two non-homologous DNA segments (see, e.g. Cahill et al. (2006), *Front. Biosci.* 11:1958-1976). DNA repair by non-homologous end-joining is error-prone and frequently results in the untemplated addition or deletion of DNA sequences at the site of repair. Thus, in certain embodiments, a rationally-designed meganuclease can be used to produce a double-stranded break at a meganuclease recognition sequence within a target sequence to disrupt a gene (e.g., by introducing base insertions, base deletions, or frame-shift mutations) by non-homologous end-joining. In other embodiments, an exogenous nucleic acid lacking homology to or substantial sequence similarity with the target sequence may be captured at the site of a meganuclease-stimulated double-stranded DNA break by non-homologous end-joining (see, e.g., Salomon et al. (1998), *EMBO J.* 17:6086-6095). The process of non-homologous end-joining occurs in both eukaryotes and prokaryotes such as bacteria.

As used herein, the term "sequence of interest" means any nucleic acid sequence, whether it codes for a protein, RNA, or regulatory element (e.g., an enhancer, silencer, or promoter sequence), that can be inserted into a genome or used to replace a genomic DNA sequence using a meganuclease protein. Sequences of interest can have heterologous DNA sequences that allow for tagging a protein or RNA that is expressed from the sequence of interest. For instance, a protein can be tagged with tags including, but not limited to, an epitope (e.g., c-myc, FLAG) or other ligand (e.g., poly-His). Furthermore, a sequence of interest can encode a fusion protein, according to techniques known in the art (see, e.g., Ausubel et al., *Current Protocols in Molecular Biology*, Wiley 1999). In some embodiments, the sequence of interest is flanked by a DNA sequence that is recognized by the recombinant meganuclease for cleavage. Thus, the flanking sequences are cleaved allowing for proper insertion of the sequence of interest into genomic recognition sequences cleaved by the recombinant meganuclease. In some embodiments, the entire sequence of interest is homologous to or has substantial sequence similarity with a target sequence in the genome such that homologous recombination effectively replaces the target sequence with the sequence of interest. In other embodiments, the sequence of interest is flanked by DNA sequences with homology to or substantial sequence similarity with the target sequence such that homologous recombination inserts the sequence of interest within the genome at the locus of the target sequence. In some embodiments, the sequence of interest is substantially identical to the target sequence except for mutations or other modifications in the meganuclease recognition sequence such that the meganuclease can not cleave the target sequence after it has been modified by the sequence of interest.

As used herein with respect to both amino acid sequences and nucleic acid sequences, the terms "percentage similarity" and "sequence similarity" refer to a measure of the degree of similarity of two sequences based upon an alignment of the sequences which maximizes similarity between aligned amino acid residues or nucleotides, and which is a function of the number of identical or similar residues or nucleotides, the number of total residues or nucleotides, and the presence and length of gaps in the sequence alignment. A variety of algorithms and computer programs are available for determining sequence similarity using standard parameters. As used herein, sequence similarity is measured using the BLASTp program for amino acid sequences and the BLASTn program for nucleic acid sequences, both of which are available through the National Center for Biotechnology Information (www.ncbi.nlm.nih.gov/), and are described in, for example, Altschul et al. (1990), *J. Mol. Biol.* 215:403-410; Gish and States (1993), *Nature Genet.* 3:266-272; Madden et al. (1996), *Meth. Enzymol.* 266:131-141; Altschul et al. (1997), *Nucleic Acids Res.* 25:33 89-3402); Zhang et al. (2000), *J. Comput. Biol.* 7 (1-2): 203-14. As used herein, percent similarity of two amino acid sequences is the score based upon the following parameters for the BLASTp algorithm: word size=3; gap opening penalty=−11; gap extension penalty=−1; and scoring matrix=BLOSUM62. As used herein, percent similarity of two nucleic acid sequences is the score based upon the following parameters for the BLASTn algorithm: word size=11; gap opening penalty=−5; gap extension penalty=−2; match reward=1; and mismatch penalty=−3.

As used herein with respect to modifications of two proteins or amino acid sequences, the term "corresponding to" is used to indicate that a specified modification in the first protein is a substitution of the same amino acid residue as in the modification in the second protein, and that the amino acid position of the modification in the first proteins corresponds to or aligns with the amino acid position of the modification in the second protein when the two proteins are subjected to standard sequence alignments (e.g., using the BLASTp program). Thus, the modification of residue "X" to amino acid "A" in the first protein will correspond to the modification of residue "Y" to amino acid "A" in the second protein if residues X and Y correspond to each other in a sequence alignment, and despite the fact that X and Y may be different numbers.

As used herein, the recitation of a numerical range for a variable is intended to convey that the invention may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values ≥0 and ≤2 if the variable is inherently continuous.

As used herein, unless specifically indicated otherwise, the word "or" is used in the inclusive sense of "and/or" and not the exclusive sense of "either/or."

2. Single-Chain Meganucleases Derived from LAGLIDADG (SEQ ID NO: 55) Subunits

Structural comparisons of natural mono- and di-LAGLIDADG (SEQ ID NO: 55) meganucleases reveal that the N-terminal subunits of di-LAGLIDADG (SEQ ID NO: 55) meganucleases tend to be smaller than mono-LAGLIDADG (SEQ ID NO: 55) monomers. The consequence of this is that, in the case of di-LAGLIDADG (SEQ ID NO: 55) meganucleases, the end (C-terminus) of the N-terminal subunit is much closer to the start (N-terminus) of the C-terminal subunit. This means that a relatively short (e.g., 5-20 amino acid) linker is sufficient to join the two subunits. In the case of mono-LAGLIDADG (SEQ ID NO: 55) meganucleases, the C-terminus of one monomer is generally very far (approximately 48 Å in the case of I-CreI) from the N-terminus of the second monomer. Therefore, fusing a pair of mono-LAGLIDADG (SEQ ID NO: 55) meganucleases into a single polypeptide requires a longer (e.g., >20 amino acid) peptide linker which can span this distance. An alternative method, in which the N-terminal subunit is truncated at a point spatially closer to the start of the C-terminal subunit has been reported previously (Epinat et al. (2003), Nucleic Acids Res. 31:2952-62; WO 2003/078619), but produces little if any functional heterodimer, as shown in Example 1 below. An extensive discussion regarding the difficulty associated with producing a functional single-chain meganuclease derived from I-CreI can be found in Fajardo-Sanchez et al. (2008), Nucleic Acids Res. 36:2163-2173.

2.1 Fusion Points for I-CreI

A series of truncation mutants were made in which either wild-type I-CreI or an engineered variant of I-CreI which had been altered with respect to its DNA cleavage site preference (designated "CCR2", SEQ ID NO: 31; see WO 2007/047859) were terminated prior to the natural C-terminal amino acid, Pro 163 (Table 1). The mutant homodimers were expressed in E. coli, purified, and incubated with either the wild-type recognition sequence (SEQ ID NOs: 34-35) or the CCR2 recognition sequence (SEQ ID NOs: 32-33) to test for cleavage activity.

Wild-type I-CreI was found to be active when truncated at residue 148 or further C-terminal residues, but inactive when truncated at residue 141 or further N-terminal residues. Therefore, at least some of residues 141 through 147, or conservative substitutions of those residues, are required for wild-type activity. Similarly, CCR2 was found to be active when truncated at residue 151 or further C-terminal residues, but inactive when terminated at residue 148 or further N-terminal residues. Therefore, at least some of residues 148 through 150, or conservative substitutions of those residues, are required for CCR2 activity. The difference between the wild-type I-CreI and the rationally-designed CCR2 meganuclease is presumably due to a reduction in the structural stability of the CCR2 meganuclease such that it is more sensitive to further destabilization by a premature C-terminal truncation. These truncation results are consistent with a publication from Prieto et al. in which it was found that the C-terminal loop of I-CreI (amino acids 138-142) is essential for cleavage activity (Prieto et al. (2007), Nucl. Acids Res. 35:3262-3271). Taken together, these results indicate that some residues near the C-terminus of I-CreI are essential for DNA-binding and/or catalytic activity and methods for single-chain meganuclease production that truncate an I-CreI subunit prior to approximately residue 142 (e.g., Epinat et al. (2003), Nucl. Acids Res. 31:2952-62; WO 2003/078619) are unlikely to yield a single-chain meganuclease in which both LAGLIDADG (SEQ ID NO: 55) subunits are catalytically active.

TABLE 1

I-CreI Truncation Mutants

| C-terminal amino acid | Wild-type activity | CCR2 activity |
|---|---|---|
| Asp-153 | + | + |
| Val-151 | + | + |
| Val-148 | + | − |
| Arg-141 | − | − |
| Asn-136 | − | − |
| Val-129 | − | − |
| Ile-109 | − | − |
| Leu-95 | − | − |

Therefore, in accordance with the present invention, the N-terminal fusion point (i.e., between the N-terminal I-CreI subunit and the linker) should lie at or C-terminal to residue 142 of the N-terminal subunit, including any of positions 142-151, or any position C-terminal to residue 151. Residues 154-163 of I-CreI are unstructured (Jurica et al. (1998), Mol. Cell 2:469-476) and, therefore, inclusion of these residues will increase the flexibility and, possibly, structural instability of the resultant single-chain meganuclease. Conversely, if it is determined that less flexibility and greater structural stability are desired or required, fusion points at residues 142-153 can be chosen.

When the C-terminal LAGLIDADG (SEQ ID NO: 55) subunit of a single-chain meganuclease is derived from I-CreI, the C-terminal fusion point of the linker will be toward the N-terminus of the I-CreI sequence. Residues 7, 8 and 9 are of particular interest as C-terminal fusion points in I-CreI because these residues (1) are structurally conserved among LAGLIDADG (SEQ ID NO: 55) meganuclease family members and, therefore, may provide greater compatibility in forming heterodimers with other LAGLIDADG (SEQ ID NO: 55) family members, and (2) initiate an alpha-helix containing the conserved LAGLIDADG (SEQ ID NO: 55) motif that is involved in catalytic function. However, fusion points N-terminal to residue 7, including any of residues 1-6, can also be employed in accordance with the invention.

The following I-CreI N-terminal and C-terminal fusion points were chosen for further experimentation, but should not be regarded as limiting the scope of the invention:

TABLE 2

I-CreI Fusion Points

| N-terminal fusion point | C-terminal fusion point |
|---|---|
| Val-151 | Lys-7 |
| Leu-152 | Asp-8 |
| Asp-153 | Phe-9 |

2.2 Linkers for Single-Chain Meganucleases Derived from I-CreI

For the purpose of linking a pair of I-CreI monomers into a single polypeptide, two general classes of linker were considered: (1) an unstructured linker lacking secondary structure; and (2) a structured linker having secondary structure. Examples of unstructured linkers are well known in the art, and include artificial sequences with high Gly and Ser content, or repeats. Structured linkers are also well known in the art, and include those designed using basic principles of protein folding (e.g., Aurora and Rose (1998), Protein Sci. 7:21-38; Fersht, Structure and Mechanism in Protein Science, W.H. Freeman 1998).

The invention was validated using a pair of rationally-designed I-CreI monomers called "LAM1" (SEQ ID NO: 36) and "LAM2" (SEQ ID NO: 37). These rationally-designed endonucleases were produced using the methods described in WO 2007/047859 and they are characterized therein. As will be apparent to those of skill in the art, however, the LAM1 and LAM2 monomers are merely exemplary of the many monomers which can be employed, including wild-type mono-LAGLIDADG (SEQ ID NO: 55) subunits, N-terminally and/or C-terminally truncated wild-type mono-LAGLIDADG (SEQ ID NO: 55) subunits, N-terminally and/or C-terminally truncated wild-type di-LAGLIDADG (SEQ ID NO: 55) subunits, and rationally designed modifications of any of the foregoing.

One exemplary monomer, LAM1, differs by 7 amino acids from wild-type I-CreI and recognizes the half site:

```
5'-TGCGGTGTC-3'

3'-ACGCCACAG-5'
```

Thus, the LAM1 homodimer recognizes the palindromic recognition sequence (where each N is unconstrained):

```
                                          (SEQ ID NO: 40)
5'-TGCGGTGTCNNNNNGACACCGCA-3'

(SEQ ID NO: 41)
3'-ACGCCACAGNNNNNCTGTGGCGT-5'
```

The other exemplary monomer, LAM2, differs by 5 amino acids from wild-type I-CreI and recognizes the half-site:

```
5'-CAGGCTGTC-3'

3'-GTCCGACAG-5'
```

Thus, the LAM2 homodimer recognizes the palindromic recognition sequence (where each N is unconstrained):

```
                                          (SEQ ID NO: 44)
5'-CAGGCTGTCNNNNNGACAGCCTG-3'

(SEQ ID NO: 45)
3'-GTCCGACAGNNNNNCTGTCGGAC-5'
```

A heterodimer comprising one LAM1 monomer and one LAM2 monomer ("LAM1/LAM2 heterodimer") thus recognizes the hybrid recognition sequence:

```
                                          (SEQ ID NO: 56)
5'-TGCGGTGTCNNNNNGACAGCCTG-3'

(SEQ ID NO: 57)
3'-ACGCCACAGNNNNNCTGTCGGAC-5'
```

2.2.1 Flexible Linkers for Single-Chain Meganucleases

A variety of highly-flexible peptide linkers are known in the art and can be used in accordance with the invention. For example, and without limitation, peptide linkers comprising repeating Gly-Ser-Ser units are known to be unstructured and flexible (Fersht, *Structure and Mechanism in Protein Science*, W.H. Freeman 1998). Linkers with this and similar compositions are frequently used to fuse protein domains together (e.g., single-chain antibodies (Mack et al. (1995), *Proc. Nat. Acad. Sci.* 92:7021-7025); growth factor receptors (Ueda et al. (2000), *J. Immunol. Methods* 241:159-170); enzymes (Brodelius et al. (2002), 269:3570-3577); and DNA-binding and nuclease domains (Kim et al. (1996), *Proc. Nat. Acad. Sci.* 93:1156-1160).

As a general matter, the flexible linker can include any polypeptide sequence which does not form stable secondary structures under physiological conditions. In some embodiments, the linkers include a high percentage (e.g., >50%, 60%, 70%, 80% or 90%, or generally, 50%-100%) of polar uncharged residues (i.e., Gly, Ser, Cys, Asn, Gln, Tyr, Thr). In addition, in some embodiments, the linkers include a low percentage of large hydrophobic residues (i.e., Phe, Trp, Met). The linkers may include repeats of varying lengths (e.g., $(SG)_n$, $(GSS)_n$, $(SGGS)_n$ (SEQ ID NO: 58)), may include random sequences, or may include combinations of the two.

Thus, in accordance with the invention, a set of single-chain fusions between LAM1 and LAM2 were produced in which a highly-flexible peptide linker covalently joined the N-terminal (LAM1) subunit to the C-terminal (LAM2) subunit using Val-151 or Asp-153 as the N-terminal fusion point and Phe-9 as the C-terminal fusion point. The single-chain proteins were expressed in *E. coli*, purified, and tested for the ability to cleave a hybrid DNA site comprising one LAM1 half-site and one LAM2 half-site (SEQ ID NOs: 46 and 47). Cleavage activity was rated on a four point scale: − no detectable activity; + minimal activity; ++ medium activity; +++ activity comparable to the LAM1/LAM2 heterodimer produced by co-expression of the two monomers in *E. coli* prior to endonuclease purification. The proteins were also evaluated by SDS-PAGE to determine the extent to which the linker region was proteolyzed during expression or purification to release the two subunits.

TABLE 3

Single-Chain I-CreI Meganucleases with Gly-Ser Linkers

| Linker number | N-term. fusion pt. | C-term. fusion pt. | Linker sequence | SEQ ID NO: | Activity | Linker proteolysis |
|---|---|---|---|---|---|---|
| 1 | Val-151 | Phe-9 | $(GSS)_7G$ | 59 | − | − |
| 2 | Val-151 | Phe-9 | $(GSS)_8G$ | 60 | − | − |
| 3 | Val-151 | Phe-9 | $(GSS)_9G$ | 61 | + | + |
| 4 | Val-151 | Phe-9 | $(GSS)_{10}G$ | 62 | ND | +++ |
| 5 | Val-151 | Phe-9 | $(GSS)_{11}G$ | 63 | ND | +++ |
| 6 | Val-151 | Phe-9 | $(GSS)_9GG$ | 64 | + | + |
| 7 | Val-151 | Phe-9 | $(GSS)_9GSG$ | 65 | + | + |
| 8 | Asp-153 | Phe-9 | $(GSS)_9G$ | 61 | + | + |

The results indicated that flexible linkers, such as the Gly-Ser linkers in Table 3, are suitable for single-chain meganuclease production provided that the length is appropriate (see also Example 2). For example, referring to Table 3, single-chain meganucleases including linkers 1 and 2, comprising 22 and 25 total amino acids, respectively, did not exhibit any detectable cleavage activity with the fusion points tested. SDS-PAGE indicated that these meganucleases were intact and were not degraded by proteases, leading to the conclusion that these single-chain meganucleases were structurally stable but functionally constrained by linkers that were too short to allow the individual LAGLIDADG (SEQ ID NO: 55) subunits to adopt the necessary conformation for DNA binding and/or catalysis. Linkers 3, 6, 7, and 8, comprising 28, 29, 30, and 28 amino acids, respectively, all exhibited low levels of cleavage activity. SDS-PAGE indicated that a small amount (5%-10%) of each was proteolyzed into individual subunits while the majority had a molecular weight corresponding to the full-length single-chain meganuclease (~40 kilodaltons). Numbers 3 and 8 have the same linker sequence but N-terminal fusion points at Val-151 and Asp-153, respectively. Both single-chain meganucleases exhibited comparable levels of activity, indicating that the precise fusion point is not critical in this instance. Finally, linkers 4 and 5, comprising 31 and 34 amino acids, respectively, yielded no detectable single-chain meganuclease when purified from *E. coli*. These linkers were completely proteolyzed to the individual LAM1 and/or LAM2 subunits as detected by SDS-PAGE and, therefore, the cleavage activity of these meganucleases was not investigated further.

These results led us to conclude that Gly-Ser linkers are acceptable for the production of single-chain meganucleases based upon the LAGLIDADG (SEQ ID NO: 55) subunit of the mono-LAGLIDADG (SEQ ID NO: 55) meganuclease I-CreI and the particular fusion points employed, provided that the linkers are greater than 25 and less than 31 amino acids in length. For I-CreI-based single-chain meganucleases with these fusion points, shorter linkers prevent catalysis while longer linkers are unstable and prone to clipping by proteases.

The effects of varying the fusions points on the acceptable linker lengths can be determined empirically by routine experimentation and/or predicted based upon three-dimensional modeling of the protein structures. Significantly, as a fusion point is moved either N-terminally or C-terminally, it may move either closer or farther from the other fusion point depending upon the secondary and tertiary structure of the protein near the fusion point. Thus, for example, moving the N-terminal fusion point in the C-terminal direction (e.g., from residue 150 to residue 155 for an N-terminal subunit) does not necessarily result in the N-terminal fusion point being physically closer to the C-terminal fusion point because, for example, the N-terminal residues in that region may be part of a secondary/tertiary structure that is pointing either towards or away from the C-terminal fusion point. Thus, moving an N-terminal fusion point in either the N-terminal or C-terminal direction, or moving a C-terminal fusion point in either the N-terminal or C-terminal direction, can result in a shift in the range of acceptable linker lengths toward either longer or shorter linkers. That shift, however, is readily determined, as shown by the experiments reported herein, by routine experimentation and/or three-dimensional modeling.

Thus, in some embodiments, useful flexible linkers have lengths of greater than 25 residues and less than 31 residues (including all values in between), as shown in Table 3 for a single-chain meganuclease based on two I-CreI LAGLIDADG (SEQ ID NO: 55) subunits. In other embodiments, however, employing different LAGLIDADG (SEQ ID NO: 55) subunits and/or different fusion points, useful flexible linkers can have lengths greater than 15 and less than 40 residues (including all values in between), provided that the linkers are not extensively proteolyzed and that the single-chain meganuclease retains DNA-binding and cleavage activity as determined by the simple assays described herein.

2.2.2 Designed, Structured Linkers for Single-Chain Meganucleases

In an effort to produce single-chain I-CreI-based meganucleases with nuclease activity comparable to the natural dimeric enzyme which are both stable enough for long-term storage and resistant to proteolysis, linkers having stable secondary structures can be used to covalently join subunits. A search of the Protein Databank (www.rcsb.org) did not reveal any structurally-characterized LAGLIDADG (SEQ ID NO: 55) proteins with linkers suitable for spanning the great distance (approx. 48 Å) between the identified N- and C-terminal fusion points in I-CreI. Therefore, known first principles governing protein structure (e.g., Aurora and Rose (1998), *Protein Sci.* 7:21-38; Fersht, *Structure and Mechanism in Protein Science*, W.H. Freeman 1998) were employed to produce a set of linkers expected to have structural elements suitable for joining the two subunits. Specifically, it was postulated that a suitable linker would comprise (listed from N-terminal fusion point to C-terminal fusion point):

(1) Loop 1. This structural element starts at the N-terminal fusion point and reverses the direction of the peptide chain back on itself (a 180° turn). The sequence can be 3-8 amino acids and can include at least one glycine residue or, in some embodiments, 2-3 glycines. This structural element can be stabilized by introducing a "C-capping" motif to terminate the C-terminal α-helix of I-CreI and initiate the subsequent turn. The helix cap motif is typically described as beginning with a hydrophobic amino acid in the final turn of the helix (Aurora and Rose (1998), *Protein Sci.* 7:21-38). The C-cap can take any of the forms listed in Table 4:

TABLE 4

C-capping Motifs

| Number | Motif |
|---|---|
| 1 | $h_1$xpx-Gh |
| 2 | $h_1$xpx-nxhx |
| 3 | $h_1$xpx-nxph |
| 4 | $h_1$xxx-Gphx |
| 5 | $h_1$xxx-Gpph |
| 6 | $h_1$xxx-Pppph |
| 7 | $h_1$xxx-Ppph | where h=a hydrophobic amino acid (Ala, Val, Leu, Ile, Met, Phe, Trp, Thr, or Cys); p=a polar amino acid (Gly, Ser, Thr, Asn, Gln, Asp, Glu, Lys, Arg); n=a non-β-branched amino acid (not Val, Ile, Thr, or Pro); x=any amino acid from the h or p group; G=glycine; and P=proline. Note that Thr appears in both groups h and p because its side chain has both hydrophobic (methyl group) and polar (hydroxyl) functional groups. The hyphen designates the end of the α-helix and $h_1$ is a hydrophobic amino acid in the final turn of the helix (i.e., a hydrophobic amino acid 0-4 amino acids prior to the N-terminal fusion point). In the case of I-CreI, h1 is typically Val-151 or Leu-152. Thus, an example of motif 7 is the sequence $V_{151}L_{152}D_{153}$S-PGSV (SEQ ID NO: 66) (see, for example, Table 6, Linker 9).

(2) α-helix 1. Following Loop 1, this first α-helix in the linker is designed to run anti-parallel to the C-terminal helix in I-CreI (amino acids 144-153) on the outside face of the protein for a distance of approximately 30 Å. This segment should be 10-20 amino acids in length, should not contain any glycine or proline amino acids outside of the N- and C-capping motifs (below), and alternate hydrophobic and polar amino acids with 3-4 amino acid periodicity so as to bury one face of the helix (the hydrophobic face) against the surface of the N-terminal I-CreI subunit while exposing the other face to solvent. The helix could, for example, take the form pphpphhpphpp where p is any polar amino acid and h is any hydrophobic amino acid but neither is glycine or proline such as the sequence SQASSAASSASS (SEQ ID NO: 67) (see, for example, Table 6, Linker 9). Numerous algorithms are available to determine the helical propensity of a peptide sequence (e.g., BMERC-PSA, bmerc-www.b-u.edu/psa/; NNPREDICT, alexander.compbio.ucsf.edu/~nomi/nnpredict.html; PredictProtein, www.predictprotein.org) and any of these can be used to produce a sequence of the appropriate length that can be expected to adopt α-helical secondary structure. Alternatively, this helix sequence could be derived from a peptide sequence known to adopt α-helical secondary structure in an existing natural or designed protein. Numerous examples of such peptide sequences are available in the Protein Databank (www.rcsb.org).

In addition, it may be desirable to initiate the α-helix with an N-capping motif to stabilize its structure (Aurora and Rose (1998), *Protein Sci.* 7:21-38). This motif spans the loop—α-helix junction and typically has one of the forms shown in Table 5:

TABLE 5

N-capping Motifs

| Number | Motif |
|---|---|
| 1 | h-xpxhx |
| 2 | h-xxpph |
| 3 | hp-xpxhx |
| 4 | hp-xxpph |
| 5 | hpp-xpxhx |
| 6 | hpp-xxpph | where the designations are as in Table 4 above and the hyphen represents the junction between the loop and the helix. An example of motif number 2 is the sequence L-SPSQA (SEQ ID NO: 68) (see, for example, Table 6, Linker 9).

(3) Turn 1. Following α-helix 1, a short, flexible peptide sequence is introduced to turn the overall orientation of the peptide chain by approximately 90° relative to the orientation of α-helix 1. This sequence can be 3-8 amino acids in length and can contain 1 or, in some embodiments, 2-3 glycines. This sequence can also contain a C-cap such as one of the motifs in Table 4 to stabilize α-helix 1 and initiate the turn. An example is the sequence ASSS-PGSGI (SEQ ID NO: 69) (see, for example, Table 6, Linker 9) which conforms to C-capping motif number 6. In this case, the sequence ASSS (SEQ ID NO: 70) is the final turn of α-helix 1 while the sequence PGSGI (SEQ ID NO: 71) is Turn 1.

(4) α-helix 2. This helix follows Turn 1 and is designed to lie at the surface of I-CreI in a groove created at the interface between the LAGLIDADG (SEQ ID NO: 55) subunits. The surface of this groove comprises primarily amino acids 94-100 and 134-139 of the N-terminal subunit and amino acids 48-61 of the C-terminal subunit.

α-helix 2 can be designed to be shorter than α-helix 1 and can comprise 1-3 turns of the helix (4-12 amino acids). α-helix 2 can have the same overall amino acid composition as α-helix 1 and can also be stabilized by the addition of an N-capping motif of Table 5. The sequence I-SEALR (SEQ ID NO: 72) is an example (see, for example, Table 6, Linker 9) that conforms to N-capping motif number 1. Linker 9 incorporates a relatively short α-helix 2 comprising the sequence SEALRA (SEQ ID NO: 73) which is expected to make approximately two turns. Experiments with different linker α-helix 2 sequences have demonstrated the importance of helical register in this region of the linker. The addition of a single amino acid (e.g., A, Linker 11), two amino acids (e.g., AS, Linker 12), or three amino acids (e.g., ASS, Linker 13) prior to the termination of α-helix 2 with a glycine amino acid can result in single-chain I-CreI proteins that are unstable and precipitate within moments of purification from E. coli (Table 6). In contrast, the addition of four amino acids (e.g., ASSA (SEQ ID NO: 74), linker 14), which is expected to make one full additional turn and restore the helical register to that of Linker 1 is stable and active.

(5) Loop 2. This loop terminates α-helix 2 and turns the peptide chain back on itself to join with the C-terminal I-CreI subunit at the C-terminal fusion point. As with Loop 1, this sequence can be 3-8 amino acids in length and can contain one or more glycines. It can also contain a C-capping motif from Table 4 to stabilize α-helix 2. For example, the sequence ALRA-GA (SEQ ID NO: 75) from Linker 9 conforms to C-capping motif number 1. In addition, this segment can begin an N-cap on the N-terminal α-helix (amino acids 7-20) of the C-terminal I-CreI subunit. For example the sequence T-$KSK_7E_8F_9$ (SEQ ID NO: 76) from Linker 9 conforms to N-capping motif number 2. In this instance, the C-terminal fusion point is Lys-7. In other cases, the fusion point can be moved further into the second subunit (for example to amino acids 8 or 9), optionally with the addition of 1-2 amino acids to Loop 2 to compensate for the change in helical register as the C-terminal fusion point is moved. For example, linkers 15-23 in Table 6 below have Glu-8 as the C-terminal fusion point and all have an additional amino acid in Loop 2 relative to Linkers 1-6.

TABLE 6

Linkers for Single-Chain I-CreI

| # | CFP | Linker Sequence | SEQ ID NO: | Activity | ppt |
|---|---|---|---|---|---|
| 9 | K7 | SLPGSVGGLSPSQASSAASSASSSPGSGISEALRAGATKS | 77 | +++ | − |
| 10 | K7 | SLPGSVGGLSPSQASSAASSASSSPGSGISEALRAGGATKS | 78 | +++ | − |
| 11 | K7 | SLPGSVGGLSPSQASSAASSASSSPGSGISEALRAAGGATKS | 79 | ND | ++ |
| 12 | K7 | SLPGSVGGLSPSQASSAASSASSSPGSGISEALRAASGGATKS | 80 | ND | ++ |
| 13 | K7 | SLPGSVGGLSPSQASSAASSASSSPGSGISEALRAASSGGATKS | 81 | ND | ++ |
| 14 | K7 | SLPGSVGGLSPSQASSAASSASSSPGSGISEALRAASSAGGATKS | 82 | +++ | − |
| 15 | E8 | SLPGSVGGLSPSQASSAASSASSSPGSGISEALRAGATKEF | 83 | ++ | + |
| 16 | E8 | SLPGSVGGISPSQASSAASSASSSPGSGTSEAPRAGATKEF | 84 | ++ | − |

TABLE 6-continued

Linkers for Single-Chain I-CreI

| # | CFP | Linker Sequence | SEQ ID NO: | Activity | ppt |
|---|-----|-----------------|------------|----------|-----|
| 17 | E8 | SLPGSVGGLSPSQASSAASSASSSPGSGTSEATRAGATKEF | 85 | ++ | + |
| 18 | E8 | SLPGSLGGLSPSQASSAASSASSSPGSGPSEALRAGATKEF | 86 | ++ | + |
| 19 | E8 | SLPGSVGGVSPSQASSAASSASSSPGSGVSEASRAGATKEF | 87 | ++ | + |
| 20 | E8 | SLPGSVGGLSPSQASSAASSASSSPGSGLSEALRAGATKEF | 88 | ++ | + |
| 21 | E8 | SLPGSLGGISPSQASSAASSASSSPGSGSSEASRAGATKEF | 89 | ++ | − |
| 22 | E8 | SPGSVGGVSPSQASSAASSASSSPGSGISEATRAGATKEF | 90 | ++ | − |
| 23 | E8 | SLPGSLGGVSPSQASSAASSPGSGTSEAPRAGATKEF | 91 | ND | ++ |
| 24 | E8 | SLPGSVGGLSPSQASSAASSPGSGISEAIRAGATKEF | 92 | ++ | − |
| 25 | E8 | SLPGSLGGVSPSQASSAASSASSAASSPGSGASEASRAGATKEF | 93 | ++ | − |

Employing the principles described above, the set of linkers outlined in Table 6 were developed. A set of single-chain I-CreI meganucleases incorporating the linkers between LAM1 and LAM2 subunits was constructed and each was tested for activity against the LAM1/LAM2 hybrid recognition sequence. In all cases, the N-terminal fusion point was Asp-153 of LAM1 and the C-terminal fusion point was either Lys-7 or Glu-8 (denoted in the "CFP" column) of LAM2. Cleavage activity was rated on a four point scale: − no detectable activity; + minimal activity; ++ medium activity; +++ activity comparable to the LAM1/LAM2 heterodimer produced by co-expression of the two monomers in E. coli prior to endonuclease purification. Immediately following purification, the single-chain meganucleases were centrifuged (2100 g for 10 minutes) to pellet precipitated protein (indicative of structural instability) and the amount of precipitate (ppt) observed was scored: − no precipitate; + slight precipitate; ++ significant precipitate. Those protein samples that precipitated to a significant degree could not be assayed for cleavage activity.

Single-chain meganucleases each of these linkers except for 11-13 and 23 (which were not investigated) ran as a single band of the desired molecular weight (~40 kilodaltons) on an SDS-PAGE gel, indicative of resistance to proteolytic cleavage of the linker sequence. In at least one case (Linker 9), the single-chain LAM meganuclease could be stored at 4° C. in excess of 4 weeks without any evidence of degradation or loss of cleavage activity. Moreover, a number of single-chain LAM endonucleases (9, 10, and 14) cleaved the hybrid LAM1/LAM2 recognition sequence with efficiency comparable to the purified LAM1/LAM2 heterodimer, indicating that fusing I-CreI subunits using these linkers does not significantly impair endonuclease activity (see Example 2).

In stark contrast to the purified LAM1/LAM2 heterodimer (which is, in fact, a mixture of homo- and heterodimers), the single-chain LAM meganucleases incorporating the linkers in Table 6 cleave the hybrid site much more efficiently than either of the palindromic sequences (see Example 2). The palindromic sequences are typically cut with <5% efficiency relative to the hybrid site. This unintended cleavage of the palindromic DNA sites could be due to (1) homo-dimerization of LAM1 or LAM2 subunits from a pair of different single-chain proteins, (2) sequential nicking of both strands of the palindromic sequence by a single subunit (LAM1 or LAM2) within the single-chain meganuclease, or (3) minute amounts of homodimeric LAM1 or LAM2 that form following proteolytic cleavage of the single-chain meganuclease into its individual subunits (although SDS-PAGE results make this latter explanation unlikely). Although the single-chain I-CreI meganucleases maintain some activity toward palindromic DNA sites, the activity is so disproportionately skewed in favor of the hybrid site that this approach represents a very significant improvement over existing methods.

3. Single-Chain Meganucleases Derived from I-MsoI

I-MsoI is a close structural homolog of I-CreI and similar methods have been presented for redesigning the DNA-binding specificity of this meganuclease (WO 2007/047859). The method presented above for the production of a single-chain I-CreI meganuclease can be directly applied to I-MsoI. Amino acids Phe-160, Leu-161, and Lys-162 of I-MsoI are structurally homologous to, respectively, Val-151, Leu-152, and Asp-153 of I-CreI. These amino acids, therefore, can be selected as the N-terminal fusion points for I-MsoI. In addition, The X-ray crystal structure of I-MsoI reveals that amino acids 161-166 naturally act as a C-cap and initiate a turn at the C-terminus of the protein which reverses the direction of the peptide chain. Thus, Ile-66 can be selected as the N-terminal fusion point provided that the linker is shortened at its N-terminus to remove the C-cap portion of Loop 1. Pro-9, Thr-10, and Glu-11 of I-MsoI are structurally homologous to, respectively, Lys-7, Glu-8, and Phe-9 of I-CreI and can be selected as C-terminal fusion points for I-MsoI (Table 7). In addition, because the sequence $L_7Q_8P_9T_{10}E_{11}A_{12}$ (SEQ ID NO: 94) of I-MsoI forms a natural N-cap (motif 2 from Table 5), Leu-7 can be included as a fusion point.

TABLE 7

I-MsoI Fusion Points

| N-terminal fusion points | C-terminal fusion points |
|---|---|
| Phe-160 | Leu-7 |
| Leu-161 | Pro-9 |
| Lys-162 | Thr-10 |
| Ile-166 | Glu-11 |

Any of the linkers in Tables 3 or 6 can be used for the production of single-chain I-MsoI endonucleases. For example, Linker 9 from Table 6 may be used to join a pair of I-MsoI subunits into a functional single-chain meganuclease using Lys-162 and Pro-9 as fusion points. In one embodiment, Pro-9 is changed to a different amino acid (e.g., alanine or glycine) because proline is structurally constraining. This is analogous to selecting Thr-10 as the C-terminal fusion point and adding an additional amino acid to the C-terminus of the linkers listed in Tables 3 or 6. For example Linkers 26 and 27 from Table 8 are identical to Linker 9 from Table 6 except for the addition of a single amino acid at the C-terminus to account for a change in C-terminal fusion point from Pro-9 (structurally homologous to I-CreI Lys-7) to Thr-10 (structurally homologous to I-CreI Glu-8).

In another embodiment, as described in Example 4, a single-chain meganuclease derived from I-Mso can also be successfully produced using a linker sequence selected from Linker 28-30 from Table 8 in which I-166 is selected as the N-terminal fusion point and Leu-7 is selected as the C-terminal fusion point. Because I-166 is selected as the N-terminal fusion point, the C-cap portion of Loop 1 (corresponding to the first 6 amino acids of each of the linkers from Table 6) can be removed. In addition, α-helix 1 of Linkers 28-30 are lengthened by 3 amino acids (AAS, underlined in Table 8) relative to the linkers listed in Table 6, corresponding to one additional turn of the helix. Using Linkers 28-30 and the specified fusion points, it is possible to produce protease-resistant, high-activity single-chain meganucleases comprising a pair of I-Mso-derived subunits (see Example 4).

4. Single-Chain Meganucleases Derived from I-CeuI

I-CeuI is a close structural homolog of I-CreI and similar methods have been presented for redesigning the DNA-binding specificity of this meganuclease (WO 2007/047859). The method presented above for the production of a single-chain I-CreI meganuclease can be directly applied to I-CeuI. Amino acids Ala-210, Arg-211, and Asn-212 of I-CeuI are structurally homologous to, respectively, Val-151, Leu-152, and Asp-153 of I-CreI. These amino acids, therefore, can be selected as the N-terminal fusion points for I-CeuI. Ser-53, Glu-54, and Ser-55 of I-CeuI are structurally homologous to, respectively, Lys-7, Glu-8, and Phe-9 of I-CreI and can be selected as C-terminal fusion points for I-CeuI (Table 9).

TABLE 9

I-CeuI Fusion Points

| N-terminal fusion points | C-terminal fusion points |
|---|---|
| Ala-210 | Ser-53 |
| Arg-211 | Glu-54 |
| Asn-212 | Ser-55 |

Any of the linkers in Tables 3 or 6 can be effective for the production of single-chain I-CeuI endonucleases. For example, I-CeuI subunits can be joined by Linker 9 from Table 6 using Asn-212 as the N-terminal fusion point and Ser-53 as the C-terminal fusion point.

The C-terminal fusion points selected for I-CeuI result in the removal of amino acids 1-52 from the C-terminal I-CeuI subunit. Structural analyses (Spiegel et al. (2006), *Structure* 14:869-880) reveal that these amino acids form a structured domain that rests on the surface of I-CeuI and buries a substantial amount of hydrophobic surface area contributed by amino acids 94-123. It is possible, therefore, that removing this N-terminal domain will destabilize the C-terminal I-CeuI subunit in the single-chain meganuclease. To mitigate this possibility, the hydrophobic amino acids that would be exposed by the removal of this N-terminal domain can be mutated to polar amino acids (e.g., non-β-branched, hydro-

TABLE 8

Linkers for Single-Chain I-MsoI

| # | NFP | CFP | Linker Sequence | SEQ ID NO: | Activity | ppt |
|---|---|---|---|---|---|---|
| 26 | K162 | T10 | PGSVGGLSPSQASSAASSASSSPGSGISEALRAGATKSA | 95 | ++ | − |
| 27 | K162 | T10 | PGSVGGLSPSQASSAASSASSSPGSGISEALRAGATKSG | 96 | ++ | − |
| 28 | I166 | L7 | GGASPSQASSAASSASSAASSPGSGISEALRAASSLASKPGST | 97 | +++ | − |
| 29 | I166 | L7 | GGASPSQASSAASSASSAASSPGSGISEALRAASSPGST | 98 | +++ | − |
| 30 | I166 | L7 | GGASPSQASSAASSASSAASSPGSGPSEALRAASSFASKPGST | 99 | +++ | − | phobic amino acids can be mutated to Ser while β-branched, hydrophobic amino acids can be mutated to Thr). For example, Leu-101, Tyr-102, Leu-105, Ala-121, and Leu-123 can be mutated to Ser while Val-95, Val-98, and Ile-113 can be mutated to Thr.

Alternatively, the N-terminal domain of the C-terminal I-CeuI subunit can be left largely intact and joined to the N-terminal subunit via a truncated linker. This can be accomplished using Lys-7, Pro-8, Gly-9, or Glu-10 (SEQ ID NO: 100) as a C-terminal fusion point. The linker can be a flexible Gly-Ser linker (e.g., Linker 3 from Table 3) truncated by approximately 50% of its length (i.e., (GSS) 4G (SEQ ID NO: 101) or (GSS) 5G (SEQ ID NO: 102)). Alternatively, the linker can be any of the linkers from Table 6 truncated within Turn 1. Thus, using Linker 9 from Table 6 as an example, a single-chain I-CeuI meganuclease can be made with the following composition:

```
                                           (SEQ ID NO: 103)
N-term. subunit N212-SLPGSVGGLSPSQASSAASSASSSPGS-
G9 C-term. subunit
```

5. Single-Chain Meganucleases Derived from Two Different LAGLIDADG (SEQ ID NO: 55) Family Members This invention also enables the production of single-chain meganucleases in which each of the subunits is derived from a different natural LAGLIDADG (SEQ ID NO: 55) domain. "Different," as used in this description, refers to LAGLIDADG (SEQ ID NO: 55) subunits that are not derived from the same natural LAGLIDADG (SEQ ID NO: 55) family member. Thus, as used in this description, rationally-designed LAGLIDADG (SEQ ID NO: 55) subunits from the same family member (e.g., two I-CreI subunits that have been genetically engineered with respect to DNA cleavage specificity) are not considered "different". Specifically, the invention enables the production of single-chain meganucleases comprising an N-terminal subunit derived from a mono-LAGLIDADG (SEQ ID NO: 55) meganuclease (e.g., I-CreI, I-MsoI, or I-CeuI) linked to a C-terminal subunit derived from a different mono-LAGLIDADG (SEQ ID NO: 55) meganuclease or either of the two LAGLIDADG (SEQ ID NO: 55) domains from a di-LAGLIDADG (SEQ ID NO: 55) meganuclease. For example, a single-chain meganuclease can be produced comprising an N-terminal I-CreI subunit, which may or may not have been rationally-designed with regard to DNA recognition site specificity, linked to a C-terminal I-MsoI subunit which also may or may not have been rationally-designed with regard to DNA recognition site specificity.

In the cases of I-CreI, I-MsoI, and I-CeuI, the desirable fusion points and linkers are as described above. For example, a single-chain I-CreI to I-MsoI fusion can be produced using Linker 9 from Table 6 to join I-CreI Asp-153 to I-MsoI Thr-10. Table 9 lists potential C-terminal fusion points for individual LAGLIDADG (SEQ ID NO: 55) domains from the di-LAGLIDADG (SEQ ID NO: 55) meganucleases I-SceI, I-DmoI, and I-AniI.

TABLE 10

C-terminal Fusion Points for di-LAGLIDADG (SEQ ID NO: 55) Meganuclease Subunits

| I-SceI N-terminal (31-123) | I-SceI C-terminal (132-225) | I-AniI N-terminal (3-125) | I-AniI C-terminal (135-254) | I-DmoI N-terminal (8-98) | I-DmoI C-terminal (104-178) |
|---|---|---|---|---|---|
| I-31 | Y-132 | D3 | S-135 | S-8 | R-104 |
| E-32 | L-133 | L4 | Y-136 | G-9 | E-105 |
| Q-33 | T-134 | Y6 | F-137 | I-10 | Q-106 |

The fusion points listed in Tables 7, 9 and 10 are based on structure comparisons between the meganuclease in question and I-CreI in which amino acid positions which are structurally homologous to the I-CreI fusion points were identified. Fusion points can also be identified in LAGLIDADG (SEQ ID NO: 55) subunits which have not been structurally characterized using protein sequence alignments to I-CreI. This is particularly true of C-terminal fusion points which can be readily identified in any LAGLIDADG (SEQ ID NO: 55) subunit based upon the location of the conserved LAGLIDADG (SEQ ID NO: 55) motif. The amino acids which are 4-6 residues N-terminal of the start of the LAGLIDADG (SEQ ID NO: 55) motif are acceptable C-terminal fusion points.

Because the dimerization interfaces between subunits from different LAGLIDADG (SEQ ID NO: 55) endonucleases vary, the subunits may not associate into functional "heterodimers" despite being covalently joined as a single polypeptide. To promote association, the interface between the two subunits can be rationally-designed, as described in WO 2007/047859. At its simplest, this involves substituting interface residues from one subunit onto another. For example, I-CreI and I-MsoI differ in the interface region primarily at I-CreI Glu-8 (which is a Thr in the homologous position of I-MsoI, amino acid 10) and Leu-11 (which is an Ala in the homologous position of I-MsoI, amino acid 13). Thus, I-CreI and I-MsoI subunits can be made to interact effectively by changing Glu-8 and Leu-11 of the I-CreI subunit to Thr and Ala, respectively, or by changing Thr-10 and Ala-13 of the I-MsoI subunit to Glu and Leu, respectively.

Techniques such as computational protein design algorithms can also be used to rationally-design the subunit interfaces. Such methods are known in the art. For example, Chevalier et al. used a computational algorithm to redesign the interface between I-CreI and the N-terminal LAGLIDADG (SEQ ID NO: 55) domain of I-DmoI to enable the two to interact (Chevalier et al. (2002), *Mol. Cell* 10:895-905). Taking these results into account, a single-chain meganuclease comprising an N-terminal subunit derived from I-CreI and a C-terminal subunit derived from the N-terminal LAG[[A]]LIDADG (SEQ ID NO: 55) domain of I-DmoI can be produced by (1) selecting an N-terminal fusion point in I-CreI from Table 2, (2) selecting a C-terminal fusion point in I-DmoI from Table 10, (3) selecting a linker from Table 6 (or designing a similar linker based on the rules provided), and (4) incorporating the mutations L11A, F16I, K96N, and L97F into the I-CreI subunit and the mutations I19W, H51F, and L55R into the I-DmoI subunit as proposed by Chevalier et al.

Alternatively, empirical methods such as directed evolution can be used to engineer the interface between two different LAGLIDADG (SEQ ID NO: 55) subunits. Such methods are known in the art. For example, genetic libraries can be produced in which specific amino acids in the subunit interface are randomized, and library members which permit the interaction between the two subunits are screened experimentally. Such screening methods are known in the art (e.g., Sussman et al. (2004), *J. Mol. Biol.* 342:31-41; Chames et al. (2005), *Nucl. Acids Res.* 33: e178; Seligman et al. (2002), *Nucl. Acids Res.* 30:3870-9, Arnould et al. (2006), *J. Mol. Biol.* 355:443-58) and can be conducted to test for the ability of a single-chain meganuclease comprising two different LAGLIDADG (SEQ ID NO: 55) subunits to cleave a hybrid DNA site within a yeast or bacterial cell.

6. Single-Chain Meganucleases with Altered DNA-Cleavage Specificity, Activity, and/or DNA-Binding Affinity The invention can be used to produce single-chain meganucleases comprising individual LAGLIDADG (SEQ ID NO: 55) subunits that have been genetically-engineered with respect to DNA-cleavage specificity using a variety of methods. Such methods include rational-design (e.g., WO 2007/047859), computational design (e.g., Ashworth et al. (2006), *Nature* 441:656-659), and genetic selection (Sussman et al. (2004), *J. Mol. Biol.* 342:31-41; Chames et al. (2005), *Nucl. Acids Res.* 33: e178; Seligman et al. (2002), *Nucl. Acids Res.* 30:3870-9, Arnould et al. (2006), *J. Mol. Biol.* 355:443-58). Such meganucleases can be targeted to DNA sites that differ from the sites recognized by wild-type meganucleases. The invention can also be used to join LAGLIDADG (SEQ ID NO: 55) subunits that have been rationally-designed to have altered activity (e.g., WO 2007/047859; Arnould et al. (2007), *J. Mol. Biol* 371 (1): 49-65) or DNA-binding affinity as described in WO 2007/047859.

7. Methods of Producing Recombinant Cells and Organisms

Aspects of the present invention further provide methods for producing recombinant, transgenic or otherwise genetically-modified cells and organisms using single-chain meganucleases. Thus, in certain embodiments, recombinant single-chain meganucleases are developed to specifically cause a double-stranded break at a single site or at relatively few sites in the genomic DNA of a cell or an organism to allow for precise insertion(s) of a sequence of interest by homologous recombination. In other embodiments, recombinant meganucleases are developed to specifically cause a double-stranded break at a single site or at relatively few sites in the genomic DNA of a cell or an organism to either (a) allow for rare insertion(s) of a sequence of interest by non-homologous end-joining or (b) allow for the disruption of the target sequence by non-homologous end-joining. As used herein with respect to homologous recombination or non-homologous end-joining of sequences of interest, the term "insertion" means the ligation of a sequence of interest into a chromosome such that the sequence of interest is integrated into the chromosome. In the case of homologous recombination, an inserted sequence can replace an endogenous sequence, such that the original DNA is replaced by exogenous DNA of equal length, but with an altered nucleotide sequence. Alternatively, an inserted sequence can include more or fewer bases than the sequence it replaces.

Therefore, in accordance with this aspect of the invention, the recombinant organisms include, but are not limited to, monocot plant species such as rice, wheat, corn (maize) and rye, and dicot species such as legumes (e.g., kidney beans, soybeans, lentils, peanuts, peas), alfalfa, clover, tobacco and *Arabidopsis* species. In addition, the recombinant organisms can include, but are not limited to, animals such as humans and non-human primates, horses, cows, goats, pigs, sheep, dogs, cats, guinea pigs, rats, mice, lizards, fish and insects such as *Drosophila* species. In other embodiments, the organism is a fungus such as a *Candida, Neurospora* or *Saccharomyces* species.

In some embodiments, the methods of the invention involve the introduction of a sequence of interest into a cell such as a germ cell or stem cell that can become a mature recombinant organism or allow the resultant genetically-modified organism to give rise to progeny carrying the inserted sequence of interest in its genome.

Meganuclease proteins can be delivered into cells to cleave genomic DNA, which allows for homologous recombination or non-homologous end-joining at the cleavage site with a sequence of interest, by a variety of different mechanisms known in the art. For example, the recombinant meganuclease protein can introduced into a cell by techniques including, but not limited to, microinjection or liposome transfections (see, e.g., Lipofectamine™, Invitrogen Corp., Carlsbad, CA). The liposome formulation can be used to facilitate lipid bilayer fusion with a target cell, thereby allowing the contents of the liposome or proteins associated with its surface to be brought into the cell. Alternatively, the enzyme can be fused to an appropriate uptake peptide such as that from the HIV TAT protein to direct cellular uptake (see, e.g., Hudecz et al. (2005), *Med. Res. Rev.* 25:679-736).

Alternatively, gene sequences encoding the meganuclease protein are inserted into a vector and transfected into a eukaryotic cell using techniques known in the art (see, e.g., Ausubel et. al., *Current Protocols in Molecular Biology*, Wiley 1999). The sequence of interest can be introduced in the same vector, a different vector, or by other means known in the art.

Non-limiting examples of vectors for DNA transfection include virus vectors, plasmids, cosmids, and YAC vectors. Transfection of DNA sequences can be accomplished by a variety of methods known to those of skill in the art. For instance, liposomes and immunoliposomes are used to deliver DNA sequences to cells (see, e.g., Lasic et al. (1995), *Science* 267:1275-76). In addition, viruses can be utilized to introduce vectors into cells (see, e.g., U.S. Pat. No. 7,037, 492). Alternatively, transfection strategies can be utilized such that the vectors are introduced as naked DNA (see, e.g., Rui et al. (2002), *Life Sci.* 71 (15): 1771-8).

General methods for delivering nucleic acids into cells include: (1) chemical methods (Graham et al. (1973), *Virology* 54 (2): 536-539; Zatloukal et al. (1992), *Ann. N.Y. Acad. Sci.,* 660:136-153; (2) physical methods such as microinjection (Capecchi (1980), *Cell* 22 (2): 479-488, electroporation (Wong et al. (1982), *Biochim. Biophys. Res. Commun.* 107 (2): 584-587; Fromm et al. (1985), *Proc. Nat'l Acad. Sci. USA* 82 (17): 5824-5828; U.S. Pat. No. 5,384,253) and ballistic injection (Johnston et al. (1994), *Methods Cell. Biol.* 43 (A): 353-365; Fynan et al. (1993), *Proc. Nat'l Acad. Sci. USA* 90 (24): 11478-11482); (3) viral vectors (Clapp (1993), *Clin. Perinatol.* 20 (1): 155-168; Lu et al. (1993), *J. Exp. Med.* 178 (6): 2089-2096; Eglitis et al. (1988), *Avd. Exp. Med. Biol.* 241:19-27; Eglitis et al. (1988), *Biotechniques* 6 (7): 608-614); and (4) receptor-mediated mechanisms (Curiel et al. (1991), *Proc. Nat'l Acad. Sci. USA* 88 (19): 8850-8854; Curiel et al. (1992), *Hum. Gen. Ther.* 3 (2): 147-154; Wagner et al. (1992), *Proc. Nat'l Acad. Sci. USA* 89 (13): 6099-6103).

In certain embodiments, a genetically-modified plant is produced, which contains the sequence of interest inserted into the genome. In certain embodiments, the genetically-modified plant is produced by transfecting the plant cell with DNA sequences corresponding to the recombinant meganuclease and the sequence of interest, which may or may not be flanked by the meganuclease recognition sequences and/or sequences substantially identical to the target sequence. In other embodiments, the genetically-modified plant is produced by transfecting the plant cell with DNA sequences corresponding to the recombinant meganuclease only, such that cleavage promotes non-homologous end-joining and disrupts the target sequence containing the recognition sequence. In such embodiments, the meganuclease sequences are under the control of regulatory sequences that allow for expression of the meganuclease in the host plant cells. These regulatory sequences include, but are not limited to, constitutive plant promoters such as the NOS promoter, chemically-inducible gene promoters such as the dexamethasone-inducible promoter (see, e.g., Gremillon et al. (2004), *Plant J.* 37:218-228), and plant tissue specific promoters such as the LGC1 promoter (see, e.g., Singh et al. (2003), *FEBS Lett.* 542:47-52).

Suitable methods for introducing DNA into plant cells include virtually any method by which DNA can be introduced into a cell, including but not limited to *Agrobacterium* infection, PEG-mediated transformation of protoplasts (Omirulleh et al. (1993), *Plant Molecular Biology,* 21:415-428), desiccation/inhibition-mediated DNA uptake, electroporation, agitation with silicon carbide fibers, ballistic injection or microprojectile bombardment, and the like.

In other embodiments, a genetically-modified animal is produced using a recombinant meganuclease. As with plant cells, the nucleic acid sequences can be introduced into a germ cell or a cell that will eventually become a transgenic organism. In some embodiments, the cell is a fertilized egg, and exogenous DNA molecules can be injected into the pro-nucleus of the fertilized egg. The micro-injected eggs are then transferred into the oviducts of pseudopregnant foster mothers and allowed to develop. The recombinant meganuclease is expressed in the fertilized egg (e.g., under the control of a constitutive promoter, such as 3-phosphoglycerate kinase), and facilitates homologous recombination of the sequence of interest into one or a few discrete sites in the genome. Alternatively, the genetically-modified animals can be obtained by utilizing recombinant embryonic stem ("ES") cells for the generation of the transgenics, as described by Gossler et al. (1986), *Proc. Natl. Acad. Sci. USA* 83:9065 9069.

In certain embodiments, a recombinant mammalian expression vector is capable of directing tissue-specific expression of the nucleic acid preferentially in a particular cell type. Tissue-specific regulatory elements are known in the art. Non-limiting examples of suitable tissue-specific promoters include the albumin promoter (liver-specific; Pinkert et al. (1987), *Genes Dev.* 1:268-277), lymphoid-specific promoters (Calame and Eaton (1988), *Adv. Immunol.* 43:235-275), in particular promoters of T cell receptors (Winoto and Baltimore (1989), *EMBO J.* 8:729-733) and immunoglobulins (Banerji et al. (1983), *Cell* 33:729-740; Queen and Baltimore (1983), *Cell* 33:741-748), neuron-specific promoters (e.g., the neurofilament promoter; Byrne and Ruddle (1989), *Proc. Natl. Acad. Sci. USA* 86:5473-5477), pancreas-specific promoters (Edlund et al. (1985), *Science* 230:912-916), and mammary gland-specific promoters (e.g., milk whey promoter; U.S. Pat. No. 4,873,316 and European Pat. Pub. EP 0 264 166). Developmentally-regulated promoters are also encompassed, e.g., the murine hox promoters (Kessel and Gruss (1990), *Science* 249:374-379) and the α-fetoprotein promoter (Campes and Tilghman (1989), *Genes Dev.* 3:537-546).

In certain embodiments, a single-chain meganuclease may be tagged with a peptide epitope (e.g., an HA, FLAG, or Myc epitope) to monitor expression levels or localization. In some embodiments, the meganuclease may be fused to a sub-cellular localization signal such as a nuclear-localization signal (e.g., the nuclear localization signal from SV40) or chloroplast or mitochondrial localization signals. In other embodiments, the meganuclease may be fused to a nuclear export signal to localize it to the cytoplasm. The meganuclease may also be fused to an unrelated protein or protein domain such as a protein that stimulates DNA-repair or homologous recombination (e.g., recA, RAD51, RAD52, RAD54, RAD57 or BRCA2).

8. Methods for Gene Therapy

Aspects of the invention allow for the use of recombinant meganuclease for gene therapy. As used herein, "gene therapy" means therapeutic treatments that comprise introducing into a patient a functional copy of at least one gene, or gene regulatory sequence such as a promoter, enhancer, or silencer to replace a gene or gene regulatory region that is defective in its structure and/or function. The term "gene therapy" can also refer to modifications made to a deleterious gene or regulatory element (e.g., oncogenes) that reduce or eliminate expression of the gene. Gene therapy can be performed to treat congenital conditions, conditions resulting from mutations or damage to specific genetic loci over the life of the patient, or conditions resulting from infectious organisms.

In some aspects of the invention, dysfunctional genes are replaced or disabled by the insertion of exogenous nucleic acid sequences into a region of the genome affecting gene expression. In certain embodiments, the recombinant meganuclease is targeted to a particular sequence in the region of the genome to be modified so as to alleviate the condition. The sequence can be a region within an exon, intron, promoter, or other regulatory region that is causing dysfunctional expression of the gene. As used herein, the term "dysfunctional expression" means aberrant expression of a gene product either by the cell producing too little of the gene product, too much of the gene product, or producing a gene product that has a different function such as lacking the necessary function or having more than the necessary function.

Exogenous nucleic acid sequences inserted into the modified region can be used to provide "repaired" sequences that normalize the gene. Gene repair can be accomplished by the introduction of proper gene sequences into the gene allowing for proper function to be reestablished. In these embodiments, the nucleic acid sequence to be inserted can be the entire coding sequence for a protein or, in certain embodiments, a fragment of the gene comprising only the region to be repaired. In other embodiments the nucleic acid sequence to be inserted comprises a promoter sequence or other regulatory elements such that mutations causing abnormal expression or regulation are repaired. In other embodiments, the nucleic acid sequence to be inserted contains the appropriate translation stop codon lacking in a mutated gene. The nucleic acid sequence can also have sequences for stopping transcription in a recombinant gene lacking appropriate transcriptional stop signals.

Alternatively, the nucleic acid sequences can eliminate gene function altogether by disrupting the regulatory sequence of the gene or providing a silencer to eliminate gene function. In some embodiments, the exogenous nucleic acid sequence provides a translation stop codon to prevent expression of the gene product. In other embodiments, the exogenous nucleic acid sequences provide transcription stop element to prevent expression of a full length RNA molecule. In still other embodiments, gene function is disrupted directly by the meganuclease by introducing base insertions, base deletions, and/or frameshift mutations through non-homologous end-joining.

In many instances, it is desirable to direct the proper genetic sequences to a target cell or population of cells that is the cause of the disease condition. Such targeting of therapeutics prevents healthy cells from being targeted by the therapeutics. This increases the efficacy of the treatment, while decreasing the potentially adverse effects that the treatment could have on healthy cells.

Delivery of recombinant meganuclease genes and the sequence of interest to be inserted into the genome to the cells of interest can be accomplished by a variety of mechanisms. In some embodiments, the nucleic acids are delivered to the cells by way of viruses with particular viral genes inactivated to prevent reproduction of the virus. Thus, a virus can be altered so that it is capable only of delivery and maintenance within a target cell, but does not retain the ability to replicate within the target cell or tissue. One or more DNA sequences can be introduced to the altered viral genome, so as to produce a viral genome that acts like a vector, and may or may not be inserted into a host genome and subsequently expressed. More specifically, certain embodiments include employing a retroviral vector such as, but not limited to, the MFG or pLJ vectors. An MFG vector is a simplified Moloney murine leukemia virus vector (MoMLV) in which the DNA sequences encoding the pol and env proteins have been deleted to render it replication defective. A pLJ retroviral vector is also a form of the MoMLV (see, e.g., Korman et al. (1987), *Proc. Nat'l Acad. Sci.,* 84:2150-2154). In other embodiments, a recombinant adenovirus or adeno-associated virus can be used as a delivery vector.

In other embodiments, the delivery of recombinant meganuclease protein and/or recombinant meganuclease gene sequences to a target cell is accomplished by the use of liposomes. The production of liposomes containing nucleic acid and/or protein cargo is known in the art (see, e.g., Lasic et al. (1995), *Science* 267:1275-76). Immunoliposomes incorporate antibodies against cell-associated antigens into liposomes, and can delivery DNA sequences for the meganuclease or the meganuclease itself to specific cell types (see, e.g., Lasic et al. (1995), *Science* 267:1275-76; Young et al. (2005), *J. Calif. Dent. Assoc.* 33 (12): 967-71; Pfeiffer et al. (2006), *J. Vasc. Surg.* 43 (5): 1021-7). Methods for producing and using liposome formulations are well known in the art, (see, e.g., U.S. Pat. Nos. 6,316,024, 6,379,699, 6,387,397, 6,511,676 and 6,593,308, and references cited therein). In some embodiments, liposomes are used to deliver the sequences of interest as well as the recombinant meganuclease protein or recombinant meganuclease gene sequences.

9. Methods for Treating Pathogen Infection

Aspects of the invention also provide methods of treating infection by a pathogen. Pathogenic organisms include viruses such as, but not limited to, herpes simplex virus 1, herpes simplex virus 2, human immunodeficiency virus 1, human immunodeficiency virus 2, variola virus, polio virus, Epstein-Barr virus, and human papilloma virus and bacterial organisms such as, but not limited to, *Bacillus anthracis, Haemophilus* species, *Pneumococcus* species, *Staphylococcus aureus, Streptococcus* species, methicillin-resistant *Staphylococcus aureus,* and *Mycoplasma* tuberculosis. Pathogenic organisms also include fungal organisms such as, but not limited to, *Candida, Blastomyces, Cryptococcus,* and *Histoplasma* species.

In some embodiments, a single-chain meganuclease can be targeted to a recognition sequence within the pathogen genome, e.g., to a gene or regulatory element that is essential for growth, reproduction, or toxicity of the pathogen. In certain embodiments, the recognition sequence may be in a bacterial plasmid. Meganuclease-mediated cleavage of a recognition sequence in a pathogen genome can stimulate mutation within a targeted, essential gene in the form of an insertion, deletion or frameshift, by stimulating non-homologous end-joining. Alternatively, cleavage of a bacterial plasmid can result in loss of the plasmid along with any genes encoded on it, such as toxin genes (e.g., *B. anthracis* Lethal Factor gene) or antibiotic resistance genes. As noted above, the meganuclease may be delivered to the infected patient, animal, or plant in either protein or nucleic acid form using techniques that are common in the art. In certain embodiments, the meganuclease gene may be incorporated into a bacteriophage genome for delivery to pathogenic bacteria.

Aspects of the invention also provide therapeutics for the treatment of certain forms of cancer. Because human viruses are often associated with tumor formation (e.g., Epstein-Barr Virus and nasopharyngeal carcinomas; Human Papilloma Virus and cervical cancer) inactivation of these viral pathogens may prevent cancer development or progression. Alternatively, double-stranded breaks targeted to the genomes of these tumor-associated viruses using single-chain meganucleases may be used to trigger apoptosis through the DNA damage response pathway. In this manner, it may be possible to selectively induce apoptosis in tumor cells harboring the viral genome.

10. Methods for Genotyping and Pathogen Identification

Aspects of the invention also provide tools for in vitro molecular biology research and development. It is common in the art to use site-specific endonucleases (e.g., restriction enzymes) for the isolation, cloning, and manipulation of nucleic acids such as plasmids, PCR products, BAC sequences, YAC sequences, viruses, and genomic sequences from eukaryotic and prokaryotic organisms (see, e.g., Ausubel et al., *Current Protocols in Molecular Biology,* Wiley 1999). Thus, in some embodiments, a single-chain meganuclease may be used to manipulate nucleic acid sequences in vitro. For example, single-chain meganucleases recognizing a pair of recognition sequences within the same DNA molecule can be used to isolate the intervening DNA segment for subsequent manipulation such as ligation into a bacterial plasmid, BAC, or YAC.

In another aspect, this invention provides tools for the identification of pathogenic genes and organisms. In one embodiment, single-chain meganucleases can be used to cleave recognition sites corresponding to polymorphic genetic regions correlated to disease to distinguish disease-causing alleles from healthy alleles (e.g., a single-chain meganuclease which recognizes the ΔF-508 allele of the human CFTR gene, see example 4). In this embodiment, DNA sequences isolated from a human patient or other organism are digested with a single-chain meganuclease, possibly in conjunction with additional site-specific nucleases, and the resulting DNA fragment pattern is analyzed by gel electrophoresis, capillary electrophoresis, mass spectrometry, or other methods known in the art. This fragmentation pattern and, specifically, the presence or absence of cleavage by the single-chain meganuclease, indicates the genotype of the organism by revealing whether or not the recognition sequence is present in the genome. In another embodiment, a single-chain meganuclease is targeted to a polymorphic region in the genome of a pathogenic virus, fungus, or bacterium and used to identify the organism. In this embodiment, the single-chain meganuclease cleaves a recognition sequence that is unique to the pathogen (e.g., the spacer region between the 16S and 23S rRNA genes in a bacterium; see, e.g., van der Giessen et al. (1994), *Microbiology* 140:1103-1108) and can be used to distinguish the pathogen from other closely-related organisms following endonuclease digest of the genome and subsequent analysis of the fragmentation pattern by electrophoresis, mass spectrometry, or other methods known in the art.

11. Methods for the Production of Custom DNA-Binding Domains

In another aspect, the invention provides single-chain DNA-binding proteins that lack endonuclease cleavage activity. The catalytic activity of a single-chain meganuclease can be eliminated by mutating amino acids involved in catalysis (e.g., the mutation of Q47 to E in I-CreI, see Chevalier et al. (2001), *Biochemistry.* 43:14015-14026); the mutation of D44 or D145 to N in I-SceI; the mutation of E66 to Q in I-CeuI; the mutation of D22 to N in I-MsoI). The inactivated meganuclease can then be fused to an effector domain from another protein including, but not limited to, a transcription activator (e.g., the GAL4 transactivation domain or the VP16 transactivation domain), a transcription repressor (e.g., the KRAB domain from the Kruppel protein), a DNA methylase domain (e.g., M.CviPI or M.SssI), or a histone acetyltransferase domain (e.g., HDAC1 or HDAC2). Chimeric proteins consisting of an engineered DNA-binding domain, most notably an engineered zinc finger domain, and an effector domain are known in the art (see, e.g., Papworth et al. (2006), *Gene* 366:27-38).

EXAMPLES

This invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below. Example 1 presents evidence that a previously disclosed method for the production of single-chain I-CreI meganucleases (Epinat et al. (2003), *Nucleic Acids Res.* 31:2952-62; WO 2003/078619) is not sufficient for the production of meganucleases recognizing non-palindromic DNA sites. Examples 2 and 3 present evidence that the method described here is sufficient to produce single-chain I-CreI meganucleases recognizing non-palindromic DNA sites using a flexible Gly-Ser linker (example 2) or a designed, structured linker (example 3). Although examples 2 and 3 below refer specifically to single-chain meganucleases based on I-CreI, single-chain meganucleases comprised of subunits derived from I-SceI, I-MsoI, I-CeuI, I-AniI, and other LAGLIDADG (SEQ ID NO: 55) meganucleases can be similarly produced and used, as described herein.

Example 1

Evaluation of the Method of Epinat et al.
1. Single Chain Meganucleases Using the Method of Epinat et al.

Epinat et al. (2003), *Nucleic Acids Res.* 31:2952-62 and WO 2003/078619 report the production of a single-chain meganuclease derived from the I-CreI meganuclease. Specifically, the authors used an 11 amino acid peptide linker derived from I-DmoI (amino acids 94-104 of I-DmoI, sequence MLERIRLFNMR (SEQ ID NO: 104)) to join an N-terminal I-CreI subunit (amino acids 1-93 of I-CreI) to a C-terminal I-CreI subunit (amino acids 8-163). This particular arrangement of N-terminal subunit-linker-C-terminal subunit was selected because it most closely mimics the domain organization of the di-LAGLIDADG (SEQ ID NO: 55) I-DmoI meganuclease. The authors evaluated the single-chain I-CreI meganuclease experimentally and found it to cleave a wild-type I-CreI recognition sequence effectively, albeit at a significantly reduced rate relative to the wild-type I-CreI homodimer.

Because the fusion protein produced by these authors comprised two otherwise wild-type subunits, both of which recognize identical DNA half-sites, it was necessary to test the single-chain meganuclease using the pseudo-palindromic wild-type DNA site. As such, it was not possible for the authors to rule out the possibility that the observed cleavage activity was not due to cleavage by an individual single-chain meganuclease but, rather, by a intermolecular dimer of two single-chain meganucleases in which one domain from each associated to form a functional meganuclease that effectively behaves like the wild-type homodimer. Indeed, a substantial portion of the N-terminal I-CreI subunit (amino acids 94-163) was removed in the production of the single-chain meganuclease reported by Epinat et al. An inspection of the three-dimensional I-CreI crystal structure (Jurica et al. (1998), *Mol. Cell* 2:469-476) reveals that this truncation results in the removal of three alpha-helices from the surface of the N-terminal subunit and the subsequent exposure to solvent of a significant amount of hydrophobic surface area. As such, the present inventors hypothesized that the N-terminal subunit from the single-chain I-CreI meganuclease of Epinat et al. is unstable and inactive and that the observed DNA cleavage activity is, in fact, due to the dimerization of the C-terminal subunits from two single-chain proteins. The protein stability problems resulting from application of the method of Epinat et al. are also discussed in Fajardo-Sanchez et al. (2008), *Nucleic Acids Res.* 36:2163-2173.
2. Design of Single-Chain LAM Meganucleases Using the Method of Epinat et al.

To more critically evaluate the method for single-chain I-CreI meganuclease production reported by Epinat et al. (Epinat et al. (2003), *Nucleic Acids Res.* 31:2952-62; WO 2003/078619), a single-chain meganuclease was produced in which the N- and C-terminal I-CreI domains recognize different DNA half-sites. The method reported in Epinat et al. was used to produce a pair of single-chain meganucleases comprising one LAM1 domain and one LAM2 domain. This "LAM1epLAM2" meganuclease (SEQ ID NO: 48) comprises an N-terminal LAM1 domain and a C-terminal LAM2 domain while "LAM2epLAM1" (SEQ ID NO: 49) comprises an N-terminal LAM2 domain and a C-terminal LAM1 domain. In total, both single-chain meganucleases differ by 11 amino acids from that reported by Epinat et al. and all amino acid changes are in regions of the enzyme responsible for DNA recognition which are not expected to affect subunit interaction.

3. Construction of Single-Chain Meganucleases.

LAM1epLAM2 and LAM2epLAM1 were produced by PCR of existing LAM1 and LAM2 genes with primers that introduce the I-DmoI linker sequence (which translates to MLERIRLFNMR (SEQ ID NO: 104)) as well as restriction enzyme sites for cloning. The two LAM subunits were cloned sequentially into pET-21a vectors with a six histidine tag (SEQ ID NO: 110) fused at the 3' end of the full-length single-chain gene for purification (Novagen Corp., San Diego, CA). All nucleic acid sequences were confirmed using Sanger Dideoxynucleotide sequencing (see, Sanger et al. (1977), *Proc. Natl. Acad. Sci. USA.* 74 (12): 5463-7).

The LAMep meganucleases were expressed and purified using the following method. The constructs cloned into a pET21a vector were transformed into chemically competent BL21 (DE3) pLysS, and plated on standard 2xYT plates containing 200 µg/ml carbanicillin. Following overnight growth, transformed bacterial colonies were scraped from the plates and used to inoculate 50 ml of 2XYT broth. Cells were grown at 37° C. with shaking until they reached an optical density of 0.9 at a wavelength of 600 nm. The growth temperature was then reduced from 37° C. to 22° C. Protein expression was induced by the addition of 1 mM IPTG, and the cells were incubated with agitation for two and a half hours. Cells were then pelleted by centrifugation for 10 min. at 6000×g. Pellets were resuspended in 1 ml binding buffer (20 mM Tris-HCL, pH 8.0, 500 mM NaCl, 10 mM imidazole) by vortexing. The cells were then disrupted with 12 pulses of sonication at 50% power and the cell debris was pelleted by centrifugation for 15 min at 14,000×g. Cell supernatants were diluted in 4 ml binding buffer and loaded onto a 200 µl nickel-charged metal-chelating Sepharose column (Pharmacia).

The column was subsequently washed with 4 ml wash buffer (20 mM Tris-HCl, pH 8.0, 500 mM NaCl, 60 mM imidazole) and with 0.2 ml elution buffer (20 mM Tris-HCl, pH 8.0, 500 mM NaCl, 400 mM imidazole). Meganuclease enzymes were eluted with an additional 0.6 ml of elution buffer and concentrated to 50-130 µl using Vivospin disposable concentrators (ISC, Inc., Kaysville, UT). The enzymes were exchanged into SA buffer (25 mM Tris-HCL, pH 8.0, 100 mM NaCl, 5 mM MgCl$_2$, 5 mM EDTA) for assays and storage using Zeba spin desalting columns (Pierce Biotechnology, Inc., Rockford, IL). The enzyme concentration was determined by absorbance at 280 nm using an extinction coefficient of 23,590 M$^{-1}$ cm$^{-1}$. Purity and molecular weight of the enzymes was then confirmed by MALDI-TOF mass spectrometry.

4. Cleavage Assays.

All enzymes purified as described above were assayed for activity by incubation with linear, double-stranded DNA substrates containing meganuclease recognition sequences. Synthetic oligonucleotides corresponding to both sense and antisense strands of the recognition sequences were annealed and were cloned into the SmaI site of the pUC19 plasmid by blunt-end ligation. The sequences of the cloned binding sites were confirmed by Sanger dideoxynucleotide sequencing. All plasmid substrates were linearized with XmnI or ScaI concurrently with the meganuclease digest. The enzyme digests contained 5 µl 0.05 µM DNA substrate, 2.5 µl 5 µM single-chain meganuclease, 9.5 µl SA buffer, and 0.5 µl XmnI or ScaI. Digests were incubated at either 37° C. for four hours. Digests were stopped by adding 0.3 mg/ml Proteinase K and 0.5% SDS, and incubated for one hour at 37° C. Digests were analyzed on 1.5% agarose and visualized by ethidium bromide staining.

5. Results

The LAMep meganucleases produced using the method of Epinat et al. were incubated with DNA substrates comprising the LAM1 palindrome (SEQ ID NOs: 40 and 41), the LAM2 palindrome (SEQ ID NOs. 44 and 45), or the LAM1/LAM2 hybrid site (SEQ ID NOs: 46 and 47). The LAM1epLAM2 single-chain meganuclease was found to cleave primarily the LAM2 palindrome whereas the LAM2epLAM1 single-chain meganuclease was found to cleave primarily the LAM1 palindrome. Neither single-chain meganuclease cleaved the hybrid site to a significant degree. These results suggest that, indeed, the method of Epinat et al. produces single-chain meganucleases that are unable to cleave non-palindromic DNA sequences. Both single-chain meganucleases were found to cleave primarily the recognition sequence corresponding to a palindrome of the half-site recognized by the C-terminal subunit, suggesting that the N-terminal subunit is inactive. Thus, the active meganuclease species characterized by Epinat et al. appears to be primarily a dimer between the C-terminal subunits of a pair of single-chain I-CreI meganucleases. Alternatively, cleavage of the palindromic DNA site may be due to sequential single strand nicking by the C-terminal subunits of different single-chain I-CreI meganucleases. In either case, in contrast to claims made by Epinat et al., the method does not produce a substantially functional single-chain I-CreI heterodimer and is generally not useful for the recognition and cleavage of non-palindromic DNA sites.

Example 2

Single-Chain I-CreI Meganucleases Produced Using a Flexible Gly-Ser Linker

1. Design of Single-Chain LAM Meganucleases Using a Gly-Ser Linker

The designed LAM1 and LAM2 endonucleases were fused into a single polypeptide using Linker 3 from Table 3. Val-151 was used as the N-terminal fusion point (to the LAM1 subunit) while Phe-9 was the C-terminal fusion point (to the LAM2 subunit). The resulting single-chain meganuclease, "LAM1gsLAM2" (SEQ ID NO: 50) was cloned into pET21a, expressed in *E. coli* and purified as described in Example 1.

2. Results

LAM1gsLAM2 was assayed for cleavage activity using the same DNA substrates and incubation conditions as described in Example 1. In contrast to results with the LAMep meganucleases, LAM1gsLAM2 was found to cleave primarily the hybrid LAM1/LAM2 recognition sequence (SEQ ID NOs: 46 and 47). The extent of cleavage is significantly reduced relative to the LAM1/LAM2 heterodimer produced by co-expressing the LAM1 and LAM2 monomers in *E. coli*. Under the same reaction conditions, the heterodimer cleaves the LAM1/LAM2 recognition sequence to completion, suggesting that the Gly-Ser linker impairs cleavage activity to some extent. Nonetheless, LAM1gsLAM2 exhibits a much stronger preference for the hybrid site over the palindromic LAM1 or LAM2 sites and, so has utility for applications in which specificity is of greater importance than activity.

Example 3

Single-Chain I-CreI Meganucleases Produced Using a Structured Linker

1. Design of Single-Chain LAM Meganucleases Using a Designed, Structured Linker

The designed LAM1 and LAM2 endonucleases were fused into a single polypeptide using Linker 9 from Table 6. Asp-153 was used as the N-terminal fusion point (to the LAM1 subunit) while Lys-7 was the C-terminal fusion point (to the LAM2 subunit). The resulting single-chain meganuclease, "LAM1desLAM2" (SEQ ID NO: 51) was cloned into pET21a, expressed in E. coli and purified as described in Example 1.

2. Results

LAM1desLAM2 was assayed for cleavage activity using the same DNA substrates and incubation conditions as described in Example 1. In contrast to results with the LAMep meganucleases, LAM1desLAM2 was found to cleave primarily the hybrid LAM1/LAM2 recognition sequence (SEQ ID NO: 46 and 47). The extent of cleavage is comparable to the LAM1/LAM2 heterodimer produced by co-expressing the LAM1 and LAM2 monomers in E. coli. These results suggest that designed, structured linkers such as Linker 9 do not interfere significantly with cleavage activity. Moreover, LAM1desLAM2 is structurally stable and maintains catalytic activity for >3 weeks when stored in SA buffer at 4° C. Importantly, LAM1desLAM2 exhibits minimal activity toward the palindromic LAM1 and LAM2 sites (SEQ ID NOS: 40 and 41 and 44 and 45), indicating that the functional species produced by the method disclosed here is primarily a single-chain heterodimer.

Example 4

Single-Chain I-MsoI Meganucleases Produced Using a Structured Linker

1. Design of Single-Chain I-MsoI Meganucleases Using a Designed, Structured Linker A pair of I-MsoI endonuclease subunits (unmodified with respect to DNA cleavage specificity) were fused into a single polypeptide using Linker 30 from Table 8. Ile-166 was used as the N-terminal fusion point while Leu-7 was the C-terminal fusion point. The resulting single-chain meganuclease, "MSOdesMSO" (SEQ ID NO: 52) was cloned into pET21a with a C-terminal 6xHis-tag (SEQ ID NO: 110) to facilitate purification. The meganuclease was then expressed in E. coli and purified as described in Example 1.

2. Results

Purified MSOdesMSO was assayed for the ability to cleave a plasmid substrate harboring the wild-type I-MsoI recognition sequence (SEQ ID NO:53 and SEQ ID NO:54 and 54) under the incubation conditions as described in Example 1. The enzyme was found to have cleavage activity comparable to the I-MsoI homodimer (which, in this case, is expected to recognize and cut the same recognition sequence as MSOdesMSO). SDS-PAGE analyses revealed that MSOdesMSO has an apparent molecular weight of ~40 kilodaltons, consistent with it being a pair of covalently joined I-MsoI subunits, and no protein degradation products were apparent. These results indicate that the invention is suitable for the production of stable, high-activity single-chain meganucleases derived from I-MsoI.

TABLE 11

| | I-CreI Modifications from WO 2007/047859 | | | | | | | | | | |
|---|---|---|---|---|---|---|---|---|---|---|---|
| | Favored Sense-Strand Base | | | | | | | | | | |
| Posn. | A | C | G | T | A/T | A/C | A/G | C/T | G/T | A/G/T | A/C/G/T |
| −1 | Y75 | R70* | K70 | Q70* | | | | T46* | | | G70 |
| | L75* | H75* | E70* | C70 | | | | | | | A70 |
| | C75* | R75* | E75* | L70 | | | | | | | S70 |
| | Y139* | H46 | E46 | Y75* | | | | | | | G46* |
| | C46* | K46* | D46* | Q75* | | | | | | | |
| | A46* | R46* | | H75* | | | | | | | |
| | | | | H139 | | | | | | | |
| | | | | Q46* | | | | | | | |
| | | | | H46* | | | | | | | |
| −2 | Q70 | E70 | H70 | Q44* | C44* | | | | | | |
| | T44* | D70 | D44* | | | | | | | | |
| | A44* | K44* | E44* | | | | | | | | |
| | V44* | R44* | | | | | | | | | |
| | I44* | | | | | | | | | | |
| | L44* | | | | | | | | | | |
| | N44* | | | | | | | | | | |
| −3 | Q68 | E68 | R68 | M68 | | H68 | | Y68 | K68 | | |
| | C24* | F68 | | C68 | | | | | | | |
| | I24* | K24* | | L68 | | | | | | | |
| | | R24* | | F68 | | | | | | | |
| −4 | A26* | E77 | R77 | | | | | S77 | | | S26* |
| | Q77 | K26* | E26* | | | | | Q26* | | | |
| −5 | | E42 | R42 | | | | K28* | C28* | | | M66 |
| | | | | | | | | Q42 | | | K66 |
| −6 | Q40 | E40 | R40 | C40 | A40 | | | | | | S40 |
| | C28* | R28* | | I40 | A79 | | | | | | S28* |
| | | | | V40 | A28* | | | | | | |
| | | | | C79 | H28* | | | | | | |
| | | | | I79 | | | | | | | |
| | | | | V79 | | | | | | | |
| | | | | Q28* | | | | | | | |

TABLE 11-continued

I-CreI Modifications from WO 2007/047859

| | | | | | | | |
|---|---|---|---|---|---|---|---|
| −7 | N30* | E38 | K38 | I38 | C38 | | H38 |
| | Q38 | K30* | R38 | L38 | | | N38 |
| | | R30* | E30* | | | | Q30* |

Favored Sense-Strand Base

| Posn. | A | Posn. | A | Posn. | A | Posn. | A | Posn. | A | Posn. | A |
|---|---|---|---|---|---|---|---|---|---|---|---|
| −8 | F33 | | E33 | | F33 | | L33 | | R32* | | R33 |
| | Y33 | | D33 | | H33 | | V33 | | | | |
| | | | | | | | I33 | | | | |
| | | | | | | | F33 | | | | |
| | | | | | | | C33 | | | | |
| −9 | | | E32 | | R32 | | L32 | | D32 | | S32 |
| | | | | | K32 | | V32 | | I32 | | N32 |
| | | | | | | | A32 | | | | H32 |
| | | | | | | | C32 | | | | Q32 |
| | | | | | | | | | | | T32 |

Bold entries are wild-type contact residues and do not constitute "modifications" as used herein.
An asterisk indicates that the residue contacts the base on the antisense strand.

TABLE 12

I-MsoI Modifications from WO 2007/047859

Favored Sense-Strand Base

| Position | A | C | G | T |
|---|---|---|---|---|
| −1 | K75* | D77 | K77 | C77 |
| | Q77 | E77 | R77 | L77 |
| | A49* | K49* | E49* | Q79* |
| | C49* | R75* | E79* | |
| | K79* | K75* | | |
| | | R79* | | |
| | | K79* | | |
| −2 | Q75 | E75 | K75 | A75 |
| | K81 | D75 | E47* | C75 |
| | C47* | R47* | E81* | V75 |
| | I47* | K47* | | I75 |
| | L47* | K81* | | T75 |
| | | R81* | | Q47* |
| | | | | Q81* |
| −3 | Q72 | E72 | R72 | K72 |
| | C26* | Y72 | K72 | Y72 |
| | L26* | H26* | Y26* | H26* |
| | V26* | K26* | F26* | |
| | A26* | R26* | | |
| | I26* | | | |
| −4 | K28 | K28* | R83 | K28 |
| | Q83 | R28* | K83 | K83 |
| | | E83 | | Q28* |
| −5 | K28 | K28* | R45 | Q28* |
| | C28* | R28* | E28* | |
| | L28* | | | |
| | I28* | | | |
| −6 | I30* | E43 | R43 | K43 |
| | V30* | E85 | K43 | I85 |
| | S30* | K30* | K85 | V85 |
| | L30* | R30* | R85 | L85 |
| | Q43 | | E30* | Q30* |
| | | | D30* | |
| −7 | Q41 | E32 | R32 | K32 |
| | | E41 | R41 | M41 |
| | | | K41 | L41 |
| | | | | I41 |
| −8 | Y35 | E32 | R32 | K32 |
| | K35 | | K32 | K35 |
| | | | K35 | |
| | | | R35 | |

TABLE 12-continued

I-MsoI Modifications from WO 2007/047859

Favored Sense-Strand Base

| Position | A | C | G | T |
|---|---|---|---|---|
| −9 | N34 | D34 | K34 | S34 |
| | H34 | E34 | R34 | C34 |
| | | S34 | H34 | V34 |
| | | | | T34 |
| | | | | A34 |

Bold entries are represent wild-type contact residues and do not constitute "modifications" as used herein.
An asterisk indicates that the residue contacts the base on the antisense strand.

TABLE 13

I-Ceu Modifications from WO 2007/047859

Favored Sense-Strand Base

| Position | A | C | G | T |
|---|---|---|---|---|
| −1 | C92* | K116* | E116* | Q116* |
| | A92* | R116* | E92* | Q92* |
| | V92* | D116* | | |
| | | K92* | | |
| −2 | Q117 | E117 | K117 | C117 |
| | C90* | D117 | R124 | V117 |
| | L90* | R174* | K124 | T117 |
| | V90* | K124* | E124* | Q90* |
| | | K90* | E90* | |
| | | R90* | D90* | |
| | | K68* | | |
| −3 | C70* | K70* | E70* | Q70* |
| | V70* | | E88* | |
| | T70* | | | |
| | L70* | | | |
| | K70* | | | |
| −4 | Q126 | E126 | R126 | K126 |
| | N126 | D126 | K126 | L126 |
| | K88* | R88* | E88* | Q88* |
| | L88* | K88* | D88* | |
| | C88* | K72* | | |
| | C72* | | | |
| | L72* | | | |
| | V72* | | | |

TABLE 13-continued

I-CeuI Modifications from WO 2007/047859

| Position | Favored Sense-Strand Base | | | |
|---|---|---|---|---|
| | A | C | G | T |
| −5 | C74* | K74* | E74* | C128 |
| | L74* | | K128 | L128 |
| | V74* | | R128 | V128 |
| | T74* | | E128 | T128 |
| −6 | Q86 | D86 | K128 | K86 |
| | E86 | | R128 | C86 |
| | R84* | | R86 | L86 |
| | K84* | | K86 | |
| | | | E84* | |
| −7 | L76* | R76* | E76* | H76* |
| | C76* | K76* | R84 | Q76* |
| | K76* | H76* | | |
| −8 | Y79 | D79 | R79 | C79 |
| | R79 | E79 | K79 | L79 |
| | Q76 | D76 | K76 | V79 |
| | | E76 | R76 | L76 |
| −9 | Q78 | D78 | R78 | K78 |
| | N78 | E78 | K78 | V78 |
| | H78 | | H78 | L78 |
| | K78 | | | C78 |
| | | | | T78 |

Bold entries are wild-type contact residues and do not constitute "modifications" as used herein.
An asterisk indicates that the residue contacts the base on the antisense strand.

TABLE 14

I-SceI Modifications from WO 2007/047859

| Position | Favored Sense-Strand Base | | | |
|---|---|---|---|---|
| | A | C | G | T |
| 4 | K50 | R50* | E50* | K57 |
| | K50* | | R57 | M57 |
| | E57 | | K57 | Q50* |
| 5 | K48 | R48* | E48* | Q48* |
| | Q102 | K48* | K102 | C102 |
| | | E102 | R102 | L102 |
| | | E59 | | V102 |
| 6 | K59 | R59* | K84 | Q59* |
| | | K59* | E59* | Y46 |
| 7 | C46* | R46* | K86 | K68 |
| | L46* | K46* | R86 | C86 |
| | V46* | E86 | E46* | L86 |
| | | | | Q46* |
| 8 | K61* | E88 | E61* | K88 |
| | S61* | R61* | R88 | Q61* |
| | V61* | H61* | K88 | H61* |
| | A61* | | | |
| | L61* | | | |
| 9 | T98* | R98* | E98* | Q98* |
| | C98* | K98* | D98* | |
| | V98* | | | |
| | L98* | | | |
| 10 | V96* | K96* | D96* | Q96* |
| | C96* | R96* | E96* | |
| | A96* | | | |
| 11 | C90* | K90* | E90* | Q90* |
| | L90* | R90* | | |
| 12 | Q193 | E165 | K165 | C165 |
| | | E193 | R165 | L165 |
| | | D193 | | C193 |
| | | | | V193 |
| | | | | A193 |
| | | | | T193 |
| | | | | S193 |
| 13 | C193* | K193* | E193* | Q193* |
| | L193* | R193* | D193* | C163 |
| | | D192 | K163 | L163 |
| | | | R192 | |
| 14 | L192* | E161 | K147 | K161 |
| | C192* | R192* | K161 | Q192* |
| | | K192* | R161 | |
| | | | R197 | |
| | | | D192* | |
| | | | E192* | |
| 15 | | E151 | K151 | C151 |
| | | | | L151 |
| | | | | K151 |
| 17 | N152* | K152* | N152* | Q152* |
| | S152* | K150* | S152* | Q150* |
| | C150* | | D152* | |
| | L150* | | D150* | |
| | V150* | | E150* | |
| | T150* | | | |
| 18 | K155* | R155* | E155* | H155* |
| | C155* | K155* | | Y155* |

Bold entries are wild-type contact residues and do not constitute "modifications" as used herein.
An asterisk indicates that the residue contacts the base on the antisense strand.

SEQUENCE LISTING

```
Sequence total quantity: 115
SEQ ID NO: 1           moltype = AA  length = 163
FEATURE                Location/Qualifiers
source                 1..163
                       mol_type = protein
                       organism = Chlamydomonas reinhardtii
SEQUENCE: 1
MNTKYNKEFL LYLAGFVDGD GSIIAQIKPN QSYKFKHQLS LTFQVTQKTQ RRWFLDKLVD   60
EIGVGYVRDR GSVSDYILSE IKPLHNFLTQ LQPFLKLKQK QANLVLKIIW RLPSAKESPD  120
KFLEVCTWVD QIAALNDSKT RKTTSETVRA VLDSLSEKKK SSP                    163

SEQ ID NO: 2           moltype = AA  length = 170
FEATURE                Location/Qualifiers
source                 1..170
                       mol_type = protein
                       organism = unidentified
SEQUENCE: 2
MTTKNTLQPT EAAYIAGFLD GDGSIYAKLI PRPDYKDIKY QVSLAISFIQ RKDKFPYLQD   60
IYDQLGKRGN LRKDRGDGIA DYTIIGSTHL SIILPDLVPY LRIKKKQANR ILHIINLYPQ  120
AQKNPSKFLD LVKIVDDVQN LNKRADELKS TNYDRLLEEF LKAGKIESSP             170
```

```
SEQ ID NO: 3            moltype = AA  length = 218
FEATURE                 Location/Qualifiers
source                  1..218
                        mol_type = protein
                        organism = Chlamydomonas sp.
SEQUENCE: 3
MSNFILKPGE KLPQDKLEEL KKINDAVKKT KNFSKYLIDL RKLFQIDEVQ VTSESKLFLA     60
GPLEGEASLN ISTKKLATSK FGLVVDPEFN VTQHVNGVKV LYLALEVFKT GRIRHKSGSN    120
ATLVLTIDNR QSLEEKVIPF YEQYVVAFSS PEKVKRVANF KALLELFNND AHQDLEQLVN    180
KILPIWDQMR KQQGQSNEGF PNLEAAQDFA RNYKKGIK                            218

SEQ ID NO: 4            moltype = AA  length = 194
FEATURE                 Location/Qualifiers
source                  1..194
                        mol_type = protein
                        organism = Desulfurococcus mobilis
SEQUENCE: 4
MHNNENVSGI SAYLLGLIIG DGGLYKLKYK GNRSEYRVVI TQKSENLIKQ HIAPLMQFLI     60
DELNVKSKIQ IVKGDTRYEL RVSSKKLYYY FANMLERIRL FNMREQIAFI KGLYVAEGDK    120
TLKRLRIWNK NKALLEIVSR WLNNLGVRNT IHLDDHRHGV YVLNISLRDR IKFVHTILSS    180
HLNPLPPERA GGYT                                                      194

SEQ ID NO: 5            moltype = AA  length = 235
FEATURE                 Location/Qualifiers
source                  1..235
                        mol_type = protein
                        organism = Saccharomyces cerevisiae
SEQUENCE: 5
MKNIKNQVM NLGPNSKLLK EYKSQLIELN IEQFEAGIGL ILGDAYIRSR DEGKTYCMQF      60
EWKNKAYMDH VCLLYDQWVL SPPHKKERVN HLGNLVITWG AQTFKHQAFN KLANLFIVNN    120
KKTIPNNLVE NYLTPMSLAY WFMDDGGKWD YNKNSTNKSI VLNTQSFTFE EVEYLVKGLR    180
NKFQLNCYVK INKNKPIIYI DSMSYLIFYN LIKPYLIPQM MYKLPNTISS ETFLK         235

SEQ ID NO: 6            moltype = AA  length = 254
FEATURE                 Location/Qualifiers
source                  1..254
                        mol_type = protein
                        organism = unidentified
SEQUENCE: 6
MSDLTYAYLV GLFEGDGYFS ITKKGKYLTY ELGIELSIKD VQLIYKIKKI LGIGIVSFRK     60
INEIEMVALR IRDKNHLKSF ILPIFEKYPM FSNKQYDYLR FRNALLSGII SLEDLPDYTR    120
SDEPLNSIES IINTSYFSAW LVGFIEAEGC FSVYKLNKDD DYLIASFDIA QRDGDILISA    180
IRKYLSFTTK VYLDKTNCSK LKVTSVRSVE NIIKFLQNAP VKLLGNKKLQ YLLWLKQLRK    240
ISRYSEKIKI PSNY                                                      254

SEQ ID NO: 7            moltype =     length =
SEQUENCE: 7
000

SEQ ID NO: 8            moltype =     length =
SEQUENCE: 8
000

SEQ ID NO: 9            moltype =     length =
SEQUENCE: 9
000

SEQ ID NO: 10           moltype =     length =
SEQUENCE: 10
000

SEQ ID NO: 11           moltype =     length =
SEQUENCE: 11
000

SEQ ID NO: 12           moltype =     length =
SEQUENCE: 12
000

SEQ ID NO: 13           moltype =     length =
SEQUENCE: 13
000

SEQ ID NO: 14           moltype =     length =
SEQUENCE: 14
000

SEQ ID NO: 15           moltype =     length =
```

```
SEQUENCE: 15
000

SEQ ID NO: 16          moltype =    length =
SEQUENCE: 16
000

SEQ ID NO: 17          moltype =    length =
SEQUENCE: 17
000

SEQ ID NO: 18          moltype =    length =
SEQUENCE: 18
000

SEQ ID NO: 19          moltype =    length =
SEQUENCE: 19
000

SEQ ID NO: 20          moltype =    length =
SEQUENCE: 20
000

SEQ ID NO: 21          moltype =    length =
SEQUENCE: 21
000

SEQ ID NO: 22          moltype =    length =
SEQUENCE: 22
000

SEQ ID NO: 23          moltype =    length =
SEQUENCE: 23
000

SEQ ID NO: 24          moltype =    length =
SEQUENCE: 24
000

SEQ ID NO: 25          moltype =    length =
SEQUENCE: 25
000

SEQ ID NO: 26          moltype =    length =
SEQUENCE: 26
000

SEQ ID NO: 27          moltype =    length =
SEQUENCE: 27
000

SEQ ID NO: 28          moltype =    length =
SEQUENCE: 28
000

SEQ ID NO: 29          moltype =    length =
SEQUENCE: 29
000

SEQ ID NO: 30          moltype =    length =
SEQUENCE: 30
000

SEQ ID NO: 31          moltype = AA   length = 163
FEATURE                Location/Qualifiers
REGION                 1..163
                       note = Description of Artificial Sequence: Synthetic
                        polypeptide
source                 1..163
                       mol_type = protein
                       organism = synthetic construct
SEQUENCE: 31
MNTKYNKEFL LYLAGFVDGD GSIKAQIKPE QNRKFKHRLE LTFQVTQKTQ RRWFLDKLVD   60
EIGVGYVYDR GSVSDYILSE IKPLHNFLTQ LQPFLKLKQK QANLVLKIIW RLPSAKESPD  120
KFLEVCTWVD QIAALNDSKT RKTTSETVRA VLDSLSEKKK SSP                   163

SEQ ID NO: 32          moltype = DNA   length = 22
FEATURE                Location/Qualifiers
misc_feature           1..22
```

```
                        note = Description of Artificial Sequence: Synthetic
                            oligonucleotide
source                  1..22
                        mol_type = other DNA
                        organism = synthetic construct
SEQUENCE: 32
aggcatctca ttagagatgc ct                                                   22

SEQ ID NO: 33           moltype = DNA  length = 22
FEATURE                 Location/Qualifiers
misc_feature            1..22
                        note = Description of Artificial Sequence: Synthetic
                            oligonucleotide
source                  1..22
                        mol_type = other DNA
                        organism = synthetic construct
SEQUENCE: 33
aggcatctct aatgagatgc ct                                                   22

SEQ ID NO: 34           moltype = DNA  length = 22
FEATURE                 Location/Qualifiers
source                  1..22
                        mol_type = genomic DNA
                        organism = Chlamydomonas reinhardtii
SEQUENCE: 34
gaaactgtct cacgacgttt tg                                                   22

SEQ ID NO: 35           moltype = DNA  length = 22
FEATURE                 Location/Qualifiers
source                  1..22
                        mol_type = genomic DNA
                        organism = Chlamydomonas reinhardtii
SEQUENCE: 35
caaaacgtcg tgagacagtt tc                                                   22

SEQ ID NO: 36           moltype = AA  length = 163
FEATURE                 Location/Qualifiers
REGION                  1..163
                        note = Description of Artificial Sequence: Synthetic
                            polypeptide
source                  1..163
                        mol_type = protein
                        organism = synthetic construct
SEQUENCE: 36
MNTKYNKEFL LYLAGFVDGD GSIIAQIDPR QCRKFKHELR LRFQVTQKTQ RRWFLDKLVD   60
EIGVGYVRDR GSVSDYILSE IKPLHNFLTQ LQPFLKLKQK QANLVLKIIW RLPSAKESPD  120
KFLEVCTWVD QIAALNDSKT RKTTSETVRA VLDSLSEKKK SSP                   163

SEQ ID NO: 37           moltype = AA  length = 163
FEATURE                 Location/Qualifiers
REGION                  1..163
                        note = Description of Artificial Sequence: Synthetic
                            polypeptide
source                  1..163
                        mol_type = protein
                        organism = synthetic construct
SEQUENCE: 37
MNTKYNKEFL LYLAGFVDGD GSIIAQIKPE QSYKFKHRLR LEFQVTQKTQ RRWFLDKLVD   60
EIGVGYVRDR GSVSDYILSE IKPLHNFLTQ LQPFLKLKQK QANLVLKIIW RLPSAKESPD  120
KFLEVCTWVD QIAALNDSKT RKTTSETVRA VLDSLSEKKK SSP                   163

SEQ ID NO: 38           moltype =   length =
SEQUENCE: 38
000

SEQ ID NO: 39           moltype =   length =
SEQUENCE: 39
000

SEQ ID NO: 40           moltype = DNA  length = 22
FEATURE                 Location/Qualifiers
misc_feature            1..22
                        note = Description of Artificial Sequence: Synthetic
                            oligonucleotide
variation               10..13
source                  1..22
                        mol_type = other DNA
                        organism = synthetic construct
SEQUENCE: 40
```

```
tgcggtgtcn nnngacaccg ca                                              22

SEQ ID NO: 41           moltype = DNA   length = 22
FEATURE                 Location/Qualifiers
source                  1..22
                        mol_type = other DNA
                        organism = synthetic construct
SEQUENCE: 41
tgcggtgtcn nnngacaccg ca                                              22

SEQ ID NO: 42           moltype =    length =
SEQUENCE: 42
000

SEQ ID NO: 43           moltype =    length =
SEQUENCE: 43
000

SEQ ID NO: 44           moltype = DNA   length = 22
FEATURE                 Location/Qualifiers
source                  1..22
                        mol_type = other DNA
                        organism = synthetic construct
variation               10..13
SEQUENCE: 44
caggctgtcn nnngacagcc tg                                              22

SEQ ID NO: 45           moltype = DNA   length = 22
FEATURE                 Location/Qualifiers
variation               10..13
source                  1..22
                        mol_type = other DNA
                        organism = synthetic construct
SEQUENCE: 45
caggctgtcn nngacagcc tg                                               22

SEQ ID NO: 46           moltype = DNA   length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 46
tgcggtgtca ttagacagcc tg                                              22

SEQ ID NO: 47           moltype = DNA   length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 47
caggctgtct aatgacaccg ca                                              22

SEQ ID NO: 48           moltype = AA   length = 260
FEATURE                 Location/Qualifiers
REGION                  1..260
                        note = Description of Artificial Sequence: Synthetic
                         polypeptide
source                  1..260
                        mol_type = protein
                        organism = synthetic construct
SEQUENCE: 48
MNTKYNKEFL LYLAGFVDGD GSIIAQIDPR QCRKFKHELR LRFQVTQKTQ RRWFLDKLVD     60
EIGVGYVRDR GSVSDYILSE IKPLHNFLTQ LQPMLERIRL FNMREFLLYL AGFVDGDGSI    120
IAQIKPEQSY KFKHRLRLEF QVTQKTQRRW FLDKLVDEIG VGYVRDRGSV SDYILSEIKP    180
LHNFLTQLQP FLKLKQKQAN LVLKIIWRLP SAKESPDKFL EVCTWVDQIA ALNDSKTRKT    240
TSETVRAVLD SLSEKKKSSP                                                260

SEQ ID NO: 49           moltype = AA   length = 260
FEATURE                 Location/Qualifiers
REGION                  1..260
                        note = Description of Artificial Sequence: Synthetic
                         polypeptide
source                  1..260
```

```
                        mol_type = protein
                        organism = synthetic construct
SEQUENCE: 49
MNTKYNKEFL LYLAGFVDGD GSIIAQIKPE QSYKFKHRLR LEFQVTQKTQ RRWFLDKLVD    60
EIGVGYVRDR GSVSDYILSE IKPLHNFLTQ LQPMLERIRL FNMREFLLYL AGFVDGDGSI   120
IAQIDPRQCR KFKHELRLRF QVTQKTQRRW FLDKLVDEIG VGYVRDRGSV SDYILSEIKP   180
LHNFLTQLQP FLKLKQKQAN LVLKIIWRLP SAKESPDKFL EVCTWVDQIA ALNDSKTRKT   240
TSETVRAVLD SLSEKKKSSP                                               260

SEQ ID NO: 50           moltype = AA  length = 334
FEATURE                 Location/Qualifiers
REGION                  1..334
                        note = Description of Artificial Sequence: Synthetic
                         polypeptide
source                  1..334
                        mol_type = protein
                        organism = synthetic construct
SEQUENCE: 50
MNTKYNKEFL LYLAGFVDGD GSIIAQIDPR QCRKFKHELR LRFQVTQKTQ RRWFLDKLVD    60
EIGVGYVRDR GSVSDYILSE IKPLHNFLTQ LQPFLKLKQK QANLVLKIIW RLPSAKESPD   120
KFLEVCTWVD QIAALNDSKT RKTTSETVRA VGSSGSSGSS GSSGSSGSSG SSGSSGSSGF   180
LLYLAGFVDG DGSIIAQIKP EQSYKFKHRL RLEFQVTQKT QRRWFLDKLV DEIGVGYVRD   240
RGSVSDYILS EIKPLHNFLT QLQPFLKLKQ KQANLVLKII WRLPSAKESP DKFLEVCTWV   300
DQIAALNDSK TRKTTSETVR AVLDSLSEKK KSSP                               334

SEQ ID NO: 51           moltype = AA  length = 350
FEATURE                 Location/Qualifiers
REGION                  1..350
                        note = Description of Artificial Sequence: Synthetic
                         polypeptide
source                  1..350
                        mol_type = protein
                        organism = synthetic construct
SEQUENCE: 51
MNTKYNKEFL LYLAGFVDGD GSIIAQIDPR QCRKFKHELR LRFQVTQKTQ RRWFLDKLVD    60
EIGVGYVRDR GSVSDYILSE IKPLHNFLTQ LQPFLKLKQK QANLVLKIIW RLPSAKESPD   120
KFLEVCTWVD QIAALNDSKT RKTTSETVRA VLDSLPGSVG GLSPSQASSA ASSASSSPGS   180
GISEALRAGA TKSKEFLLYL AGFVDGDGSI IAQIKPEQSY KFKHRLRLEF QVTQKTQRRW   240
FLDKLVDEIG VGYVRDRGSV SDYILSEIKP LHNFLTQLQP FLKLKQKQAN LVLKIIWRLP   300
SAKESPDKFL EVCTWVDQIA ALNDSKTRKT TSETVRAVLD SLSEKKKSSP              350

SEQ ID NO: 52           moltype = AA  length = 373
FEATURE                 Location/Qualifiers
REGION                  1..373
                        note = Description of Artificial Sequence: Synthetic
                         polypeptide
source                  1..373
                        mol_type = protein
                        organism = synthetic construct
SEQUENCE: 52
MTTKNTLQPT EAAYIAGFLD GDGSIYAKLI PRPDYKDIKY QVSLAISFIQ RKDKFPYLQD    60
IYDQLGKRGN LRKDRGDGIA DYTIIGSTHL SIILPDLVPY LRIKKKQANR ILHIINLYPQ   120
AQKNPSKFLD LVKIVDDVQN LNKRADELKS TNYDRLLEEF LKAGKIGGAS PSQASSAASS   180
ASSAASSPGS GPSEALRAAS SFASKPGSTL QPTEAAYIAG FLDGDGSIYA KLIPRPDYKD   240
IKYQVSLAIS FIQRKDKFPY LQDIYDQLGK RGNLRKDRGD GIADYTIIGS THLSIILPDL   300
VPYLRIKKKQ ANRILHIINL YPQAQKNPSK FLDLVKIVDD VQNLNKRADE LKSTNYDRLL   360
EEFLKAGKIE SSP                                                      373

SEQ ID NO: 53           moltype = DNA  length = 22
FEATURE                 Location/Qualifiers
source                  1..22
                        mol_type = genomic DNA
                        organism = unidentified
SEQUENCE: 53
ggaactgtct cacgacgttc tg                                             22

SEQ ID NO: 54           moltype = DNA  length = 22
FEATURE                 Location/Qualifiers
source                  1..22
                        mol_type = genomic DNA
                        organism = unidentified
SEQUENCE: 54
cagaacgtcg tgagacagtt cc                                             22

SEQ ID NO: 55           moltype = AA  length = 9
FEATURE                 Location/Qualifiers
REGION                  1..9
                        note = Description of Artificial Sequence: Synthetic peptide
source                  1..9
```

```
                        mol_type = protein
                        organism = synthetic construct
SEQUENCE: 55
LAGLIDADG                                                                9

SEQ ID NO: 56           moltype = DNA  length = 22
FEATURE                 Location/Qualifiers
variation               10..13
source                  1..22
                        mol_type = other DNA
                        organism = synthetic construct
SEQUENCE: 56
tgcggtgtcn nnngacagcc tg                                                22

SEQ ID NO: 57           moltype = DNA  length = 22
FEATURE                 Location/Qualifiers
variation               10..13
source                  1..22
                        mol_type = other DNA
                        organism = synthetic construct
SEQUENCE: 57
caggctgtcn nnngacaccg ca                                                22

SEQ ID NO: 58           moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 58
SGGS                                                                     4

SEQ ID NO: 59           moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 59
GSSGSSGSSG SSGSSGSSGS SG                                                22

SEQ ID NO: 60           moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 60
GSSGSSGSSG SSGSSGSSGS SGSSG                                             25

SEQ ID NO: 61           moltype = AA  length = 28
FEATURE                 Location/Qualifiers
REGION                  1..28
                        note = Description of Artificial Sequence: Synthetic peptide
source                  1..28
                        mol_type = protein
                        organism = synthetic construct
SEQUENCE: 61
GSSGSSGSSG SSGSSGSSGS SGSSGSSG                                          28

SEQ ID NO: 62           moltype = AA  length = 31
FEATURE                 Location/Qualifiers
REGION                  1..31
                        note = Description of Artificial Sequence: Synthetic
                         polypeptide
source                  1..31
                        mol_type = protein
                        organism = synthetic construct
SEQUENCE: 62
GSSGSSGSSG SSGSSGSSGS SGSSGSSGSS G                                      31

SEQ ID NO: 63           moltype = AA  length = 34
FEATURE                 Location/Qualifiers
REGION                  1..34
                        note = Description of Artificial Sequence: Synthetic
                         polypeptide
```

```
                       source            1..34
                                         mol_type = protein
                                         organism = synthetic construct
SEQUENCE: 63
GSSGSSGSSG SSGSSGSSGS SGSSGSSGSS GSSG                                34

SEQ ID NO: 64          moltype = AA  length = 29
FEATURE                Location/Qualifiers
REGION                 1..29
                       note = Description of Artificial Sequence: Synthetic peptide
source                 1..29
                       mol_type = protein
                       organism = synthetic construct
SEQUENCE: 64
GSSGSSGSSG SSGSSGSSGS SGSSGSSGG                                      29

SEQ ID NO: 65          moltype = AA  length = 30
FEATURE                Location/Qualifiers
REGION                 1..30
                       note = Description of Artificial Sequence: Synthetic
                        polypeptide
source                 1..30
                       mol_type = protein
                       organism = synthetic construct
SEQUENCE: 65
GSSGSSGSSG SSGSSGSSGS SGSSGSSGSG                                     30

SEQ ID NO: 66          moltype = AA  length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 66
VLDSPGSV                                                             8

SEQ ID NO: 67          moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 67
SQASSAASSA SS                                                        12

SEQ ID NO: 68          moltype = AA  length = 6
FEATURE                Location/Qualifiers
REGION                 1..6
                       note = Description of Artificial Sequence: Synthetic peptide
source                 1..6
                       mol_type = protein
                       organism = synthetic construct
SEQUENCE: 68
LSPSQA                                                               6

SEQ ID NO: 69          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 69
ASSSPGSGI                                                            9

SEQ ID NO: 70          moltype = AA  length = 4
FEATURE                Location/Qualifiers
REGION                 1..4
                       note = Description of Artificial Sequence: Synthetic peptide
source                 1..4
                       mol_type = protein
                       organism = synthetic construct
SEQUENCE: 70
ASSS                                                                 4

SEQ ID NO: 71          moltype = AA  length = 5
FEATURE                Location/Qualifiers
```

```
                                        -continued

REGION                  1..5
                        note = Description of Artificial Sequence: Synthetic peptide
source                  1..5
                        mol_type = protein
                        organism = synthetic construct
SEQUENCE: 71
PGSGI                                                                              5

SEQ ID NO: 72           moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 72
ISEALR                                                                             6

SEQ ID NO: 73           moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 73
SEALRA                                                                             6

SEQ ID NO: 74           moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 74
ASSA                                                                               4

SEQ ID NO: 75           moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 75
ALRAGA                                                                             6

SEQ ID NO: 76           moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 76
TKSKEF                                                                             6

SEQ ID NO: 77           moltype = AA  length = 40
FEATURE                 Location/Qualifiers
REGION                  1..40
                        note = Description of Artificial Sequence: Synthetic
                         polypeptide
source                  1..40
                        mol_type = protein
                        organism = synthetic construct
SEQUENCE: 77
SLPGSVGGLS PSQASSAASS ASSSPGSGIS EALRAGATKS                                        40

SEQ ID NO: 78           moltype = AA  length = 41
FEATURE                 Location/Qualifiers
REGION                  1..41
                        note = Description of Artificial Sequence: Synthetic
                         polypeptide
source                  1..41
                        mol_type = protein
                        organism = synthetic construct
SEQUENCE: 78
SLPGSVGGLS PSQASSAASS ASSSPGSGIS EALRAGGATK S                                      41
```

```
SEQ ID NO: 79           moltype = AA   length = 42
FEATURE                 Location/Qualifiers
REGION                  1..42
                        note = Description of Artificial Sequence: Synthetic
                         polypeptide
source                  1..42
                        mol_type = protein
                        organism = synthetic construct
SEQUENCE: 79
SLPGSVGGLS PSQASSAASS ASSSPGSGIS EALRAAGGAT KS                     42

SEQ ID NO: 80           moltype = AA   length = 43
FEATURE                 Location/Qualifiers
REGION                  1..43
                        note = Description of Artificial Sequence: Synthetic
                         polypeptide
source                  1..43
                        mol_type = protein
                        organism = synthetic construct
SEQUENCE: 80
SLPGSVGGLS PSQASSAASS ASSSPGSGIS EALRAASGGA TKS                    43

SEQ ID NO: 81           moltype = AA   length = 44
FEATURE                 Location/Qualifiers
REGION                  1..44
                        note = Description of Artificial Sequence: Synthetic
                         polypeptide
source                  1..44
                        mol_type = protein
                        organism = synthetic construct
SEQUENCE: 81
SLPGSVGGLS PSQASSAASS ASSSPGSGIS EALRAASSGG ATKS                   44

SEQ ID NO: 82           moltype = AA   length = 45
FEATURE                 Location/Qualifiers
REGION                  1..45
                        note = Description of Artificial Sequence: Synthetic
                         polypeptide
source                  1..45
                        mol_type = protein
                        organism = synthetic construct
SEQUENCE: 82
SLPGSVGGLS PSQASSAASS ASSSPGSGIS EALRAASSAG GATKS                  45

SEQ ID NO: 83           moltype = AA   length = 41
FEATURE                 Location/Qualifiers
REGION                  1..41
                        note = Description of Artificial Sequence: Synthetic
                         polypeptide
source                  1..41
                        mol_type = protein
                        organism = synthetic construct
SEQUENCE: 83
SLPGSVGGLS PSQASSAASS ASSSPGSGIS EALRAGATKE F                      41

SEQ ID NO: 84           moltype = AA   length = 41
FEATURE                 Location/Qualifiers
REGION                  1..41
                        note = Description of Artificial Sequence: Synthetic
                         polypeptide
source                  1..41
                        mol_type = protein
                        organism = synthetic construct
SEQUENCE: 84
SLPGSVGGIS PSQASSAASS ASSSPGSGTS EAPRAGATKE F                      41

SEQ ID NO: 85           moltype = AA   length = 41
FEATURE                 Location/Qualifiers
REGION                  1..41
                        note = Description of Artificial Sequence: Synthetic
                         polypeptide
source                  1..41
                        mol_type = protein
                        organism = synthetic construct
SEQUENCE: 85
SLPGSVGGLS PSQASSAASS ASSSPGSGTS EATRAGATKE F                      41

SEQ ID NO: 86           moltype = AA   length = 41
```

```
                                -continued
FEATURE              Location/Qualifiers
REGION               1..41
                     note = Description of Artificial Sequence: Synthetic
                      polypeptide
source               1..41
                     mol_type = protein
                     organism = synthetic construct
SEQUENCE: 86
SLPGSLGGLS PSQASSAASS ASSSPGSGPS EALRAGATKE F                        41

SEQ ID NO: 87        moltype = AA   length = 41
FEATURE              Location/Qualifiers
REGION               1..41
                     note = Description of Artificial Sequence: Synthetic
                      polypeptide
source               1..41
                     mol_type = protein
                     organism = synthetic construct
SEQUENCE: 87
SLPGSVGGVS PSQASSAASS ASSSPGSGVS EASRAGATKE F                        41

SEQ ID NO: 88        moltype = AA   length = 41
FEATURE              Location/Qualifiers
REGION               1..41
                     note = Description of Artificial Sequence: Synthetic
                      polypeptide
source               1..41
                     mol_type = protein
                     organism = synthetic construct
SEQUENCE: 88
SLPGSVGGLS PSQASSAASS ASSSPGSGLS EALRAGATKE F                        41

SEQ ID NO: 89        moltype = AA   length = 41
FEATURE              Location/Qualifiers
REGION               1..41
                     note = Description of Artificial Sequence: Synthetic
                      polypeptide
source               1..41
                     mol_type = protein
                     organism = synthetic construct
SEQUENCE: 89
SLPGSLGGIS PSQASSAASS ASSSPGSGSS EASRAGATKE F                        41

SEQ ID NO: 90        moltype = AA   length = 40
FEATURE              Location/Qualifiers
REGION               1..40
                     note = Description of Artificial Sequence: Synthetic
                      polypeptide
source               1..40
                     mol_type = protein
                     organism = synthetic construct
SEQUENCE: 90
SPGSVGGVSP SQASSAASSA SSSPGSGISE ATRAGATKEF                          40

SEQ ID NO: 91        moltype = AA   length = 37
FEATURE              Location/Qualifiers
REGION               1..37
                     note = Description of Artificial Sequence: Synthetic
                      polypeptide
source               1..37
                     mol_type = protein
                     organism = synthetic construct
SEQUENCE: 91
SLPGSLGGVS PSQASSAASS PGSGTSEAPR AGATKEF                             37

SEQ ID NO: 92        moltype = AA   length = 37
FEATURE              Location/Qualifiers
REGION               1..37
                     note = Description of Artificial Sequence: Synthetic
                      polypeptide
source               1..37
                     mol_type = protein
                     organism = synthetic construct
SEQUENCE: 92
SLPGSVGGLS PSQASSAASS PGSGISEAIR AGATKEF                             37

SEQ ID NO: 93        moltype = AA   length = 44
FEATURE              Location/Qualifiers
REGION               1..44
```

```
                        note = Description of Artificial Sequence: Synthetic
                         polypeptide
source                  1..44
                        mol_type = protein
                        organism = synthetic construct
SEQUENCE: 93
SLPGSLGGVS PSQASSAASS ASSAASSPGS GASEASRAGA TKEF                    44

SEQ ID NO: 94           moltype = AA  length = 6
FEATURE                 Location/Qualifiers
source                  1..6
                        mol_type = protein
                        organism = unidentified
SEQUENCE: 94
LQPTEA                                                               6

SEQ ID NO: 95           moltype = AA  length = 39
FEATURE                 Location/Qualifiers
REGION                  1..39
                        note = Description of Artificial Sequence: Synthetic
                         polypeptide
source                  1..39
                        mol_type = protein
                        organism = synthetic construct
SEQUENCE: 95
PGSVGGLSPS QASSAASSAS SSPGSGISEA LRAGATKSA                           39

SEQ ID NO: 96           moltype = AA  length = 39
FEATURE                 Location/Qualifiers
REGION                  1..39
                        note = Description of Artificial Sequence: Synthetic
                         polypeptide
source                  1..39
                        mol_type = protein
                        organism = synthetic construct
SEQUENCE: 96
PGSVGGLSPS QASSAASSAS SSPGSGISEA LRAGATKSG                           39

SEQ ID NO: 97           moltype = AA  length = 43
FEATURE                 Location/Qualifiers
REGION                  1..43
                        note = Description of Artificial Sequence: Synthetic
                         polypeptide
source                  1..43
                        mol_type = protein
                        organism = synthetic construct
SEQUENCE: 97
GGASPSQASS AASSASSAAS SPGSGISEAL RAASSLASKP GST                      43

SEQ ID NO: 98           moltype = AA  length = 39
FEATURE                 Location/Qualifiers
REGION                  1..39
                        note = Description of Artificial Sequence: Synthetic
                         polypeptide
source                  1..39
                        mol_type = protein
                        organism = synthetic construct
SEQUENCE: 98
GGASPSQASS AASSASSAAS SPGSGISEAL RAASSPGST                           39

SEQ ID NO: 99           moltype = AA  length = 43
FEATURE                 Location/Qualifiers
REGION                  1..43
                        note = Description of Artificial Sequence: Synthetic
                         polypeptide
source                  1..43
                        mol_type = protein
                        organism = synthetic construct
SEQUENCE: 99
GGASPSQASS AASSASSAAS SPGSGPSEAL RAASSFASKP GST                      43

SEQ ID NO: 100          moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 100
```

LPGE                                                                                        4

SEQ ID NO: 101          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 101
GSSGSSGSSG SSG                                                                              13

SEQ ID NO: 102          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 102
GSSGSSGSSG SSGSSG                                                                           16

SEQ ID NO: 103          moltype = AA  length = 29
FEATURE                 Location/Qualifiers
REGION                  1..29
                        note = Description of Artificial Sequence: Synthetic peptide
source                  1..29
                        mol_type = protein
                        organism = synthetic construct
SEQUENCE: 103
NSLPGSVGGL SPSQASSAAS SASSSPGSG                                                             29

SEQ ID NO: 104          moltype = AA  length = 11
FEATURE                 Location/Qualifiers
source                  1..11
                        mol_type = protein
                        organism = Desulfurococcus mobilis
SEQUENCE: 104
MLERIRLFNM R                                                                                11

SEQ ID NO: 105          moltype = DNA  length = 22
FEATURE                 Location/Qualifiers
misc_feature            1..22
                        note = Description of Artificial Sequence: Synthetic
                        oligonucleotide
source                  1..22
                        mol_type = other DNA
                        organism = synthetic construct
SEQUENCE: 105
tgcggtgtca ttagacaccg ca                                                                    22

SEQ ID NO: 106          moltype = DNA  length = 22
FEATURE                 Location/Qualifiers
misc_feature            1..22
                        note = Description of Artificial Sequence: Synthetic
                        oligonucleotide
source                  1..22
                        mol_type = other DNA
                        organism = synthetic construct
SEQUENCE: 106
tgcggtgtct aatgacaccg ca                                                                    22

SEQ ID NO: 107          moltype = DNA  length = 22
FEATURE                 Location/Qualifiers
misc_feature            1..22
                        note = Description of Artificial Sequence: Synthetic
                        oligonucleotide
source                  1..22
                        mol_type = other DNA
                        organism = synthetic construct
SEQUENCE: 107
caggctgtca ttagacagcc tg                                                                    22

SEQ ID NO: 108          moltype = DNA  length = 22
FEATURE                 Location/Qualifiers
misc_feature            1..22
                        note = Description of Artificial Sequence: Synthetic
                        oligonucleotide
source                  1..22

```
                        mol_type = other DNA
                        organism = synthetic construct
SEQUENCE: 108
caggctgtca ttagacagcc tg                                                 22

SEQ ID NO: 109          moltype = AA  length = 46
FEATURE                 Location/Qualifiers
REGION                  1..46
                        note = Description of Artificial Sequence: Synthetic
                         polypeptide
source                  1..46
                        mol_type = protein
                        organism = synthetic construct
SEQUENCE: 109
VLDSLPGSVG GLSPSQASSA ASSASSSPGS GISEALRAGA TKSKEF                        46

SEQ ID NO: 110          moltype = AA  length = 6
FEATURE                 Location/Qualifiers
REGION                  1..6
                        note = Description of Artificial Sequence: Synthetic 6xHis
                         tag
source                  1..6
                        mol_type = protein
                        organism = synthetic construct
SEQUENCE: 110
HHHHHH                                                                   6

SEQ ID NO: 111          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 111
ALRAGGA                                                                  7

SEQ ID NO: 112          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 112
ALRAASSAGG A                                                             11

SEQ ID NO: 113          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 113
ATRAGA                                                                   6

SEQ ID NO: 114          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 114
ASRAGA                                                                   6

SEQ ID NO: 115          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 115
AIRAGA                                                                   6
```

The invention claimed is:

1. A recombinant single-chain meganuclease comprising:
   a first LAGLIDADG (SEQ ID NO: 55) subunit comprising a polypeptide sequence having at least 85% sequence identity to residues 9-151 of a wild-type I-CreI meganuclease of SEQ ID NO: 1, said first LAGLIDADG (SEQ ID NO: 55) subunit having a first recognition half-site;
   a second LAGLIDADG (SEQ ID NO: 55) subunit comprising a polypeptide sequence having at least 85% sequence identity to residues 9-151 of a wild-type I-CreI meganuclease of SEQ ID NO: 1, said second LAGLIDADG (SEQ ID NO: 55) subunit having a second recognition half-site;
   wherein said first and second LAGLIDADG (SEQ ID NO: 55) subunits are covalently joined by a polypeptide linker such that said first LAGLIDADG (SEQ ID NO: 55) domain is N-terminal to said linker and said second LAGLIDADG (SEQ ID NO: 55) domain is C-terminal to said linker; wherein said polypeptide linker comprises 15-56 residues, and
   wherein said first and second LAGLIDADG (SEQ ID NO: 55) subunits are capable of functioning together to recognize and cleave a non-palindromic DNA sequence which is a hybrid of said first recognition half-site and said second recognition half-site.

2. The recombinant single-chain meganuclease of claim 1 wherein at least one of said LAGLIDADG (SEQ ID NO: 55) domains comprises at least one amino acid modification selected from the group consisting of A26, A28, A32, A40, A44, A46, A70, A79, C24, C28, C32, C33, C38, C40, C44, C46, C68, C70, C75, C79, D32, D33, D44, D46, D70, E26, E30, E32, E33, E38, E40, E42, E44, E46, E68, E70, E75, E77, F33, F68, G46, G70, H139, H28, H32, H33, H38, H46, H68, H70, H75, I24, I32, I33, I38, I40, I44, I79, K24, K26, K28, K30, K32, K38, K44, K46, K66, K68, K70, L32, L33, L38, L44, L68, L70, L75, M66, M68, N30, N32, N38, N44, Q26, Q28, Q30, Q32, Q38, Q40, Q42, Q44, Q46, Q68, Q70, Q75, Q77, R24, R28, R30, R32, R33, R38, R40, R42, R44, R46, R68, R70, R75, R77, S26, S28, S32, S40, S70, S77, T32, T44, T46, V32, V33, V40, V44, V79, Y139, Y33, Y68, and Y75.

3. The recombinant single-chain meganuclease of claim 1 wherein: each of said LAGLIDADG (SEQ ID NO: 55) subunits has a recognition half-site selected from the group consisting of GAAACTGTC; GACAGTTTC; CAAAACGTC; GACGTTTTG; CAGAACGTC; GACGTTCTG; GGAACTGTC; GACAGTTCC; ATAACGGTC; GACCGTTAT; TTCGCTACC; GGTAGCGAA; TAGGG; CCCTA; TAATGGGAC; GTCCCATTA; GCCGGAAC; GTTCCGGC; AACGGCC; GGCCGTT; TTTACAGA; TCTGTAAA; CTGAGGAGG; and CCTCCTCAG.

4. The recombinant single-chain meganuclease of claim 1 wherein:
   said polypeptide linker is a flexible linker.

5. The recombinant single-chain meganuclease of claim 4 wherein:
   said linker comprises 15-40 residues.

6. The recombinant single-chain meganuclease of claim 4 wherein:
   said linker comprises 25-31 residues.

7. The recombinant single-chain meganuclease of claim 4 wherein:
   at least 50% of said linker comprises polar uncharged residues.

8. The recombinant single-chain meganuclease of claim 1 wherein:
   said polypeptide linker has a stable secondary structure.

9. The recombinant single-chain meganuclease of claim 8 wherein:
   said stable secondary structure comprises at least two α-helix structures.

10. The recombinant single-chain meganuclease of claim 8 wherein:
    said stable secondary structure comprises from N-terminus to C-terminus a first loop, a first α-helix, a first turn, a second α-helix, and a second loop.

11. The recombinant single-chain meganuclease of claim 8 wherein:
    said linker comprises 23-56 residues.

* * * * *